(12) United States Patent
Toyoda et al.

(10) Patent No.: US 7,943,120 B2
(45) Date of Patent: May 17, 2011

(54) OLEFIN WAX, SILICONE-MODIFIED OLEFIN WAX, SILICONE-MODIFIED ROOM TEMPERATURE-SOLIDIFYING COMPOSITION USING THE WAX, AND COSMETICS USING THEM

(75) Inventors: Hideo Toyoda, Sodegaura (JP);
Hirotaka Uosaki, Sodegaura (JP);
Koujiro Kan, Sodegaura (JP); Shoji Ichinohe, Matsuida-machi (JP); Toru Shimizu, Chiyoda-ku (JP)

(73) Assignees: Mitsui Chemicals, Inc., Minato-Ku, Tokyo (JP); Shin-Etsu Chemical Co., Ltd, Chiyoda-Ku, Tokyo (JP)

( * ) Notice: Subject to any disclaimer, the term of this patent is extended or adjusted under 35 U.S.C. 154(b) by 227 days.

(21) Appl. No.: 12/292,724

(22) Filed: Nov. 25, 2008

(65) Prior Publication Data

US 2009/0081151 A1    Mar. 26, 2009

Related U.S. Application Data

(62) Division of application No. 10/531,377, filed as application No. PCT/JP03/13265 on Oct. 16, 2003, now abandoned.

(30) Foreign Application Priority Data

Oct. 16, 2002  (JP) ................... 2002-302202

(51) Int. Cl.
| | |
|---|---|
| *A61K 8/00* | (2006.01) |
| *A61K 8/18* | (2006.01) |
| *A61K 8/72* | (2006.01) |
| *A61K 31/74* | (2006.01) |
| *A61K 31/695* | (2006.01) |
| *A61Q 5/00* | (2006.01) |
| *A61Q 9/00* | (2006.01) |
| *A61Q 7/00* | (2006.01) |
| *A61Q 5/12* | (2006.01) |
| *A01N 55/00* | (2006.01) |

(52) U.S. Cl. .............. 424/70.12; 424/400; 424/70.1; 424/70.11; 424/78.02; 424/78.03; 424/78.08; 514/63

(58) Field of Classification Search ............... 424/400, 424/70.1, 70.11, 70.12, 78.02, 78.03, 78.08; 514/63
See application file for complete search history.

(56) References Cited

U.S. PATENT DOCUMENTS

| | | | |
|---|---|---|---|
| 5,023,388 | A | 6/1991 | Luker |
| 5,219,560 | A | 6/1993 | Suzuki et al. |
| 6,153,354 | A | 11/2000 | Katsumata et al. |
| 6,331,590 | B1 | 12/2001 | Herrmann et al. |
| 6,635,715 | B1 | 10/2003 | Datta et al. |
| 7,019,081 | B2 | 3/2006 | Datta et al. |
| 2002/0147273 | A1 | 10/2002 | Patel et al. |
| 2004/0071741 | A1 | 4/2004 | Derian |

FOREIGN PATENT DOCUMENTS

| | | |
|---|---|---|
| EP | 0 357 037 A2 | 3/1990 |
| JP | 1-501556 A | 6/1989 |
| JP | 2-64115 A | 3/1990 |
| JP | 02-132141 A | 5/1990 |
| JP | 10-500431 A | 1/1998 |
| JP | 2001-002731 A | 1/2001 |
| WO | WO 88/04674 A1 | 6/1988 |

OTHER PUBLICATIONS

Machine translation of JP-09-095514 A.*
Machine translation of JP-09-095514 to Marks et al., Aug. 4, 1997.*

* cited by examiner

*Primary Examiner* — Sreeni Padmanabhan
*Assistant Examiner* — Luke E Karpinski
(74) *Attorney, Agent, or Firm* — Buchanan Ingersoll & Rooney PC

(57) ABSTRACT

An olefin wax (A) is (i) a copolymer (A1) obtained by copolymerizing ethylene and at least one diene or a copolymer (A2) obtained by copolymerizing ethylene, at least one olefin selected from α-olefins of 3 to 12 carbon atoms and at least one diene; wherein (ii) the content of unsaturated groups per one molecule is in the range of 0.5 to 3.0 groups; (iii) the density is in the range of 870 to 980 kg/m$^3$; (iv) the melting point is in the range of 70 to 130° C.; (v) the number-average molecular weight is in the range of 400 to 5,000; and (vi) the ratio (Mw/Mn) of the weight-average molecular weight to the number-average molecular weight is not more than 4.0. A silicone-modified olefin wax can be obtained by reacting hydrogen silicone with the olefin wax (A). Cosmetics contain the silicone-modified olefin wax.

32 Claims, No Drawings

OLEFIN WAX, SILICONE-MODIFIED OLEFIN WAX, SILICONE-MODIFIED ROOM TEMPERATURE-SOLIDIFYING COMPOSITION USING THE WAX, AND COSMETICS USING THEM

CROSS REFERENCE TO RELATED APPLICATION

The present application is a divisional application of pending U.S. patent application Ser. No. 10/531,377, filed Sep. 26, 2005, which, in turn, is the National Stage Application under §371 of International Application No. PCT/JP2003/013265, filed Oct. 16, 2003, which claims priority from Japanese Application No. 2002-302202, filed Oct. 16, 2002, the entire disclosure of each of which is incorporated herein by reference.

TECHNICAL FIELD

The present invention relates to an olefin wax and a silicone-modified olefin wax obtained from the olefin wax. The invention also relates to a silicone-modified room temperature-solidifying composition containing the silicone-modified olefin wax, and to cosmetics using the silicone-modified olefin wax and/or the silicone-modified room temperature-solidifying composition. More particularly, the invention relates to cosmetics containing a specific silicone-modified olefin wax and thereby giving lightly-spreading feeling and refreshing feeling when used; having strong repellency against sweat and water; having excellent effects that softness, smoothness, emollient effect and natural gloss are imparted by paining; and having favorable temporal stability.

BACKGROUND OF THE INVENTION

In the syntheses of silicone-modified olefin waxes, use of various polyethylene oligomers, such as polyethylene oxide wax, acid anhydride-modified polyethylene wax and polyethylene oligomer having a carboxyl group at one terminal, has been heretofore studied.

In case of use of the polyethylene oxide wax, however, there is a disadvantage that a homogeneous silicone-modified polyethylene wax cannot be obtained even if the polyethylene oxide wax is modified with silicone, because the number of carboxyl groups in one molecule of the wax is 1 or less. In case of use of the acid anhydride-modified polyethylene wax, the wax is allowed to react with a double bond-containing epoxy compound, followed by addition-reaction with hydrogen silicone in the presence of a catalyst. In this case, however, since a polyethylene wax containing plural double bonds is used as an addition-reaction raw material in the addition reaction, there is a disadvantage that unless expensive hydrogen silicone having only one SiH bond in one molecule is used as hydrogen silicone to be reacted with the polyethylene wax, the silicone wax obtained after the reaction is crosslinked to gel. In case of use of the polyethylene oligomer having a carboxyl group at one terminal, there is a disadvantage that a silicone-modified polyethylene wax of high purity cannot be obtained because the polyethylene oligomer usually has a low purity of about 80%, and there is a disadvantage that a high-purity polyethylene oligomer having a carboxyl group at one terminal has a low molecular weight of about 400, so that if such a polyethylene oligomer is used, performance of a wax is not sufficiently exhibited.

Then, development of olefin waxes employable for syntheses of silicone-modified olefin waxes and high-purity silicone-modified polyethylene waxes using the olefin waxes and containing no free silicone has been desired.

Conventionally, cosmetics containing liquid oils, such as paraffin, ester, higher alcohol and glyceride, for the purpose of imparting softness, smoothness and emollient effect, have been employed. However, such conventional cosmetics cannot avoid oiliness, tackiness and oil film feeling, so that cosmetics to which silicone oils such as dimethylpolysiloxane have been blended in order to inhibit oiliness, tackiness and oil film feeling are also known.

The silicone oils have light spread, and superior smoothness and water repellency, but on the other hand, there are disadvantages that they have poor compatibility with hydrocarbon-based liquid oils, and because of low surface tension, they diffuse rapidly and have poor durability. On this account, an attempt to solidify silicone oils has been made. As materials to solidify silicone oils, a compound wherein an alkyl group is introduced into the silicone chain (Japanese Patent Laid-Open Publication No. 2-64115/1990), a compound wherein an ester group of an aliphatic alcohol or acid of 21 to 30 carbon atoms is introduced into the silicone chain (Japanese Patent Laid-Open Publication No. 10-500431/1998), acrylate silicone (Japanese Patent Laid-Open Publication No. 2-132141/1990), etc. have been proposed. In case of the compound wherein an alkyl group or a long-chain aliphatic ester group is introduced into the silicone chain, however, it is difficult to smoothly solidify the silicone oil itself, and it is general to allow a liquid oil agent, such as ester oil, triglyceride oil or paraffinic oil, to coexist in order to improve affinity of the silicone oil for waxes and thereby solidify the silicone oil. In case of the acrylate silicone, the silicone oil forms a solid even if it is used alone, but the solid is resinous and lacks smoothness required for cosmetics. That is to say, in the existing circumstances, any solid sufficiently exhibiting properties of silicone oils and having satisfactory smoothness has not been obtained yet.

OBJECT OF THE INVENTION

It is, an object of the present invention to provide an olefin wax, which is employable for synthesizing a silicone-modified olefin wax, and a high-purity silicone-modified polyolefin wax obtained by the reaction of the olefin wax with hydrogen silicone. It is another object of the invention to provide cosmetics containing the silicone-modified polyolefin wax. By virtue of inclusion of the silicone-modified polyolefin wax, the cosmetics give lightly-spreading feeling and refreshing feeling when used, specifically, they are free from tackiness and heaviness (heavy to the touch) when painted, are dry and spread lightly, and the skin after painted is dry and smooth to the touch. Further, the cosmetics have strong repellency against sweat and water, have excellent usability, specifically, ability of imparting softness, smoothness, emollient effect and natural gloss without impairing moderate transpiration of moisture by paining, and have favorable temporal stability.

SUMMARY OF THE INVENTION

The present inventors have earnestly studied to solve the above problems, and as a result, they have developed an olefin wax employable for synthesizing a silicone-modified olefin wax and a high-purity silicone-modified polyolefin wax obtained by the reaction of the olefin wax with hydrogen silicone. Further, it was found that the blend of the silicone-modified polyolefin wax into cosmetics leads to make oil agents, particularly silicone oil, smooth solids, and cosmetics having the above-mentioned properties can be obtained. Based on the finding, the present invention has been accomplished.

The olefin wax (A) according to the present invention is (i) a copolymer (A1) obtained by copolymerizing ethylene and at least one diene or a copolymer (A2) obtained by copolymerizing ethylene, at least one olefin selected from α-olefins of 3 to 12 carbon atoms and at least one diene,
and wherein (ii) the content of unsaturated groups per one molecule is in the range of 0.5 to 3.0 groups, (iii) the density is in the range of 870 to 980 kg/m³, (iv) the melting point is in the range of 70 to 130° C., (v) the number-average molecular weight is in the range of 400 to 5,000, and (vi) the ratio (Mw/Mn) of the weight-average molecular weight to the number-average molecular weight is not more than 4.0.

Preferably the olefin wax (A) of the present invention is (i) a copolymer (A3) obtained by copolymerizing ethylene and vinyl norbornene (5-vinylbicyclo[2.2.1]hept-2-ene) or a copolymer (A4) obtained by copolymerizing ethylene, at least one olefin selected from α-olefins of 3 to 12 carbon atoms and vinyl norbornene,
and wherein (ii) the content of unsaturated groups per one molecule is in the range of 0.5 to 2.0 groups, (iii) the density is in the range of 900 to 980 kg/m³, (iv) the melting point is in the range of 100 to 130° C., (v) the number-average molecular weight is in the range of 400 to 5,000, and (vi) the ratio (Mw/Mn) of the weight-average molecular weight to the number-average molecular weight is not more than 4.0.

The olefin wax (A) is preferably prepared by the use of a metallocene catalyst.

The silicone-modified olefin wax (B) according to the present invention is obtained by addition-reaction of a hydrogen silicone having one or more SiH bonds in one molecule to any of the olefin waxes (A) in the presence of a catalyst.

The silicone-modified room temperature-solidifying composition (D) according to the present invention comprises the silicone modified olefin wax (B) in an amount of 5 to 95% by mass and an oil agent (C) in an amount of 95 to 5% by mass.

The cosmetic according to the present invention comprises the silicone-modified olefin wax (B) and/or the silicon-based room temperature-solidifying composition (D).

At least a part of the oil agent (C) is preferably liquid at ordinary temperature, and at least a part of the oil agent (C) is also preferably a solid oil agent having a melting point of not lower than 50° C.

At least a part of the oil agent (C) is preferably a linear, branched or cyclic silicone oil represented by the following formula:

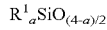
$R^1_a SiO_{(4-a)/2}$ wherein $R^1$ is a hydrogen atom, an alkyl group or a fluorine-substituted alkyl group of 1 to 30 carbon atoms, an aryl group of 6 to 30 carbon atoms or an aralkyl group of 7 to 30 carbon atoms, and "a" is a number satisfying the condition of $0 \leq a \leq 2.5$.

At least a part of the oil agent (C) preferably has a fluorine atom or an amino group.

The cosmetic of the present invention preferably further comprises water (E), and also preferably further comprises a compound (F) having an alcoholic hydroxyl group in the molecular structure. The compound (F) having an alcoholic hydroxyl group in the molecular structure is preferably a water-soluble monohydric alcohol and/or a water-soluble polyhydric alcohol.

The cosmetic of the present invention preferably further comprises a water-soluble or water-swelling high-molecular substance (G), and also preferably further comprises a powder (H1) and/or a colorant (H2). At least a part of the powder (H1) and/or the colorant (H2) is preferably a crosslinked spherical dimethylpolysiloxane fine powder having a structure wherein dimethylpolysiloxane is crosslinked, a crosslinked spherical polymethylsilsesquioxane fine powder, hydrophobic silica or a fine powder obtained by coating a surface of a crosslinked spherical polysiloxane rubber with polymethylsilsesquioxane particles. At least a part of the powder (H1) and/or the colorant (H2) also preferably has a fluorine atom.

The cosmetic of the present invention preferably further comprises a surface active agent (I). The surface active agent (I) is preferably linear or branched silicone having a polyoxyalkylene chain in the molecule and/or linear or branched silicone having a polyglycerin chain in the molecule. The surface active agent (I) also preferably has a hydrophilic-lipophilic balance (HLB) of 2 to 8.

The cosmetic of the present invention preferably further comprises a crosslinkable organopolysiloxane (J). The crosslinkable organopolysiloxane (J) is preferably a crosslinkable organopolysiloxane which contains low-viscosity silicone having a viscosity of 0.65 to 10.0 mm²/sec (25° C.) in an amount of more than its own weight to swell. The crosslinkable organopolysiloxane (J) is also preferably capable of forming a crosslinked structure by the reaction of a hydrogen atom directly bonded to a silicon atom of the organopolysiloxane (J) with a crosslinking agent having two or more vinyl reaction sites in the molecule. The crosslinkable organopolysiloxane (J) also preferably contains at least one site selected from the group consisting of polyoxyalkylene, polyglycerin, alkyl, alkenyl, aryl and fluoroalkyl in the crosslinkable molecule.

The cosmetic of the present invention preferably further comprises a silicone resin (K). The silicone resin (K) is preferably an acrylic silicone resin, and is more preferably an acrylic silicone resin containing at least one site selected from the group consisting of pyrrolidone, long-chain alkyl, polyoxyalkylene, fluoroalkyl and anions of carboxylic acids or the like in a molecule. The silicone resin (K) is also preferably a silicone network compound selected from a silicone network compound (MQ) consisting essentially of a monofunctional siloxy group and a tetrafunctional siloxy group; a silicone network compound (MDQ) consisting essentially of a monofunctional siloxy group, a bifunctional siloxy group and a tetrafunctional siloxy group; a silicone network compound (MT) consisting essentially of a monofunctional siloxy group and a trifunctional siloxy group; a silicone network compound (MDT) consisting essentially of a monofunctional siloxy group, a bifunctional siloxy group and a trifunctional siloxy group; and a silicone network compound (MDTQ) consisting essentially of a monofunctional siloxy group, a bifunctional siloxy group, a trifunctional siloxy group and a tetrafunctional siloxy group. The silicone resin (K) is also preferably a silicone network compound containing at least one site selected from the group consisting of pyrrolidone, long-chain alkyl, polyoxyalkylene, fluoroalkyl and an amino group in the molecule.

The skin care cosmetic, the make-up cosmetic, the hair cosmetic, the antiperspirant cosmetic and the ultraviolet protective cosmetic according to the present invention comprise any of the cosmetics as at least a part of constituents.

The cosmetic of the present invention is in liquid, emulsion, cream, solid, paste, gel, powder, pressed, multi-layer, mousse, spray, stick or pencil form.

DESCRIPTION OF THE PREFERRED EMBODIMENTS

The olefin wax, the silicone-modified olefin wax, the silicone-modified room temperature-solidifying composition and the cosmetics according to the invention are described in detail hereinafter.

Olefin Wax

The olefin wax can be obtained by, for example, copolymerizing an olefin with a diene using the later-described metallocene catalyst.
(Olefin)
Examples of the olefins used for preparing the olefin wax include ethylene and α-olefins of 3 to 12 carbon atoms.

Examples of the α-olefins of 3 to 12 carbon atoms include propylene, 1-butene, 1-pentene, 3-methyl-1-butene, 1-hexene, 4-methyl-1-pentene, 3-methyl-1-pentene, 1-octene, 1-decene and 1-dodecene. Of these, α-olefins of 3 to 10 carbon atoms are preferable, α-olefins of 3 to 8 carbon atoms are more preferable, and propylene, 1-butene, 1-hexene and 4-methyl-1-pentene are particularly preferable.
(Diene)
Examples of the dienes include butadiene, isoprene, 4-methyl-1,3-pentadiene, 1,3-pentadiene, 1,4-pentadiene, 1,5-hexadiene, 1,4-hexadiene, 1,3-hexadiene, 1,3-octadiene, 1,4-octadiene, 1,5-octadiene, 1,6-octadiene, 1,7-octadiene, ethylidene norbornene, vinyl norbornene (5-vinylbicyclo[2.2.1]hept-2-ene), dicyclopentadiene, 2-methyl-1,4-hexadiene, 2-methyl-1,6-octadiene, 7-methyl-1,6-octadiene, 4-ethylidene-8-methyl-1,7-nonadiene and 5,9-dimethyl-1,4,8-decatriene. Of these, vinyl norbornene, ethylidene norbornene, dicyclopentadiene, 1,4-hexadiene, butadiene, isoprene, 2-methyl-1,4-hexadiene and 2-methyl-1,6-octadiene are preferable.

Although the olefin wax is obtained by copolymerizing the above olefin and the above diene, the olefin wax (A) of the invention is preferably a copolymer of ethylene and a diene, or a copolymer of ethylene, at least one α-olefin selected from α-olefins of 3 to 12 carbon atoms and a diene.

The olefin wax (A) desirably contains constituent units derived from a diene in amounts of 0.01 to 2.0% by mol, preferably 0.1 to 0.7% by mol. When the olefin wax (A) contains constituent units derived from an α-olefin of 3 to 12 carbon atoms, their content is desired to be in the range of 0.01 to 2.0% by mol, preferably 0.1 to 0.7% by mol.

When the olefin wax (A) contains the constituent units derived from a diene in the above amount, a silicone-modified room temperature-solidifying composition having properly high polymerization activity and moderate hardness can be obtained. When the olefin wax (A) contains the constituent units derived from an α-olefin of 3 to 12 carbon atoms in the above amount, a silicone-modified room temperature-solidifying composition having moderate hardness can be obtained.

The olefin wax (A) desirably has an unsaturated group content of 0.5 to 3.0 groups/molecule, preferably 0.5 to 2.0 groups/molecule, more preferably 1.0 to 2.0 groups/molecule, on an average. When the unsaturated group content in the olefin wax (A) is in the above range, all the olefin wax (A) can be added with silicone, and hence, a silicone-modified room temperature-solidifying composition can be obtained from a small amount of a silicone-modified olefin wax.

The unsaturated group content in the olefin wax is measured in the following manner. A peak area of carbon atoms in the unsaturated portions and a peak area of all carbon atoms, both of which are determined by $^{13}$C-NMR, are compared, whereby the number M of unsaturated groups based on 1,000 carbon atoms can be obtained. The unsaturated group content per one molecule can be calculated from the formula Mn×M/14,000 using the number-average molecular weight Mn. In the present invention, the number M of unsaturated groups based on 1,000 carbon atoms is desired to be in the range of 1.4 to 70, preferably 2.8 to 35, more preferably 4 to 30.

The olefin wax (A) desirably has a density, as measured by a gradient tube density determination, of not less than 870 kg/m$^3$, preferably not less than 880 kg/m$^3$, more preferably not less than 900 kg/m$^3$, and not more than 980 kg/m$^3$, preferably not more than 970 kg/m$^3$, more preferably not more than 950 kg/m$^3$, particularly preferably not more than 920 kg/m$^3$. When the density of the olefin wax (A) is in the above range, a silicone-modified room temperature-solidifying composition having moderate hardness can be obtained.

The olefin wax (A) desirably has a melting point, as measured by a differential scanning calorimeter (DSC), of not lower than 70° C., preferably not lower than 80° C., more preferably not lower than 90° C., particularly preferably not lower than 100° C., and not higher than 140° C., preferably not higher than 130° C., more preferably not higher than 120° C., particularly preferably not higher than 110° C. When the melting point of the olefin wax (A) is in the above range, a silicone-modified room temperature-solidifying composition having moderate hardness can be obtained.

The olefin wax (A) desirably has a number-average molecular weight (Mn), as measured by gel permeation chromatography (GPC), of 400 to 5,000, preferably 800 to 5,000, more preferably 1,000 to 3,000, particularly preferably 1,500 to 2,500. When Mn of the olefin wax (A) is in the above range, a silicone-modified room temperature-solidifying composition having moderate hardness can be obtained.

The ratio (Mw/Mn) of a weight-average molecular weight to a number-average molecular weight of the olefin wax (A), as measured by GPC, is desired to be not more than 4.0, preferably not more than 3.5, more preferably not more than 3.0.

The weight-average molecular weight (Mw) and the number-average molecular weight (Mn) are values in terms of polystyrene, which are measured by gel permeation chromatography (GPC). The GPC measurement is carried out under the conditions of a temperature of 140° C. and a solvent of orthodichlorobenzene.

The olefin wax (A) desirably has a penetration hardness of not more than 15 dmm, preferably not more than 10 dmm, more preferably not more than 3 dmm, particularly preferably not more than 1 dmm. The penetration hardness can be measured in accordance with JIS K2207. When the penetration hardness of the olefin wax (A) is in the above range, a silicone-modified room temperature-solidifying composition having moderate hardness can be obtained.

The olefin wax (A) of the invention desirably has (ii) an unsaturated group content of 0.5 to 3.0 groups/molecule, (iii) a density of 870 to 980 kg/m$^3$, (iv) a melting point of 70 to 130° C., (v) a number-average molecular weight (Mn) of 400 to 5,000, and (vi) Mw/Mn (Mw: weight-average molecular weight) of not more than 4.0. The olefin wax (A) also desirably has (vii) a penetration hardness of not more than 15 dmm.

When the olefin wax (A) is obtained by copolymerization using vinyl norbornene (5-vinylbicylco[2.2.1]hept-2-ene) as a diene, this olefin wax (A) desirably has (ii) an unsaturated group content of 0.5 to 2.0 groups/molecule, (iii) a density of 900 to 980 kg/m$^3$, (iv) a melting point of 100 to 130° C., (v) a number-average molecular weight (Mn) of 400 to 5,000, and (vi) Mw/Mn (Mw: weight-average molecular weight) of not more than 4.0. This olefin wax (A) also desirably has (vii) a penetration hardness of not more than 15 dmm.

The olefin wax (A) described above can be prepared by the use of, for example, the following metallocene catalyst comprising a metallocene compound of a transition metal selected from Group 4 of the periodic table, and an organoaluminum oxy-compound and/or an ionizing ionic compound.

<Metallocene Catalyst>
(Metallocene Compound)

The metallocene compound to form the metallocene catalyst is a metallocene compound of a transition metal selected from Group 4 of the periodic table and is, for example, a compound represented by the following formula (1):

$$M^1 L_x \qquad (1)$$

wherein $M^1$ is a transition metal selected from Group 4 of the periodic table, x is an atomic valence of the transition metal $M^1$, and L is a ligand. Examples of the transition metals indicated by $M^1$ include zirconium, titanium and hafnium. L is a ligand coordinated to the transition metal $M^1$, and at least one ligand L has cyclopentadienyl skeleton. The ligand having cyclopentadienyl skeleton may have a substituent. Examples of the ligands L having cyclopentadienyl skeleton include cyclopentadienyl group; alkyl- or cycloalkyl-substituted cyclopentadienyl groups, such as methylcyclopentadienyl, ethylcyclopentadienyl, n- or i-propylcyclopentadienyl, n-, i-, sec- or t-butylcyclopentadienyl, dimethylcyclopentadienyl, methylpropylcyclopentadienyl, methylbutylcyclopentadienyl and methylbenzylcyclopentadienyl; indenyl group; 4,5,6,7-tetrahydroindenyl group; and fluorenyl group. Hydrogen of the ligand L having cyclopentadienyl skeleton may be replaced with a halogen atom or a trialkylsilyl group.

When the metallocene compound has two or more ligands having cyclopentadienyl skeleton as the ligands L, two of the ligands having cyclopentadienyl skeleton may be bonded each other through an alkylene group, such as ethylene or propylene, a substituted alkylene group, such as isopropylidene or diphenylmethylene, a silylene group, or a substituted silylene group, such as dimethylsilylene, diphenylsilylene or methylphenylsilylene.

The ligand L other than the ligand having cyclopentadienyl skeleton (ligand having no cyclopentadienyl skeleton) is, for example, a hydrocarbon group of 1 to 12 carbon atoms, an alkoxy group, an aryloxy group, a sulfonic acid-containing group ($-SO_3R^1$), a halogen atom or a hydrogen atom. $R^1$ is an alkyl group, an alkyl group substituted with a halogen atom, an aryl group, an aryl group substituted with a halogen atom, or an aryl group substituted with an alkyl group.

Example 1 of the Metallocene Compound

The metallocene compound represented by the formula (1) in which the valence of the transition metal is, for example, 4 (x=4) is more specifically represented by the following formula (2):

$$R^2{}_k R^3{}_l R^4{}_m R^5{}_n M^1 \qquad (2)$$

wherein $M^1$ is a transition metal selected from Group 4 of the periodic table, $R^2$ is a group (ligand) having cyclopentadienyl skeleton, $R^3$, $R^4$ and $R^5$ are each independently a group (ligand) having or not having cyclopentadienyl skeleton, k is an integer of 1 or more, and k+l+m+n=4.

Examples of the metallocene compounds having zirconium as $M^1$ in the formula (2) and containing at least two ligands having cyclopentadienyl skeleton include bis(cyclopentadienyl)zirconium monochloride monohydride, bis(cyclopentadienyl)zirconium dichloride, bis(1-methyl-3-butylcyclopentadienyl)zirconium-bis(trifluoromethanesulfonato) and bis(1,3-dimethylcyclopentadienyl)zirconium dichloride. Compounds given by replacing the 1,3-position-substituted cyclopentadienyl group in the above-mentioned compounds with a 1,2-position-substituted cyclopentadienyl group are also employable.

Further, bridge-containing metallocene compounds wherein at least two groups of $R^2$, $R^3$, $R^4$ and $R^5$, e.g., $R^2$ and $R^3$, in the formula (2), are each a group (ligand) having cyclopentadienyl skeleton and these at least two groups are bonded through an alkylene group, a substituted alkylene group, a silylene group, a substituted silylene group or the like are also employable as the metallocene compounds. In this case, $R^4$ and $R^5$ are each the same as the aforesaid ligand L other than the ligand having cyclopentadienyl skeleton.

Examples of the bridge-containing metallocene compounds include ethylenebis(indenyl)dimethylzirconium, ethylenebis(indenyl)zirconium dichloride, isopropylidene(cyclopentadienyl-fluorenyl)zirconium dichloride, diphenylsilylenebis(indenyl)zirconium dichloride and methylphenylsilylenebis(indenyl)zirconium dichloride.

Example 2 of the Metallocene Compound

Another example of the metallocene compound is a metallocene compound represented by the following formula (3) that is described in Japanese Patent Laid-Open Publication No. 4-268307/1992.

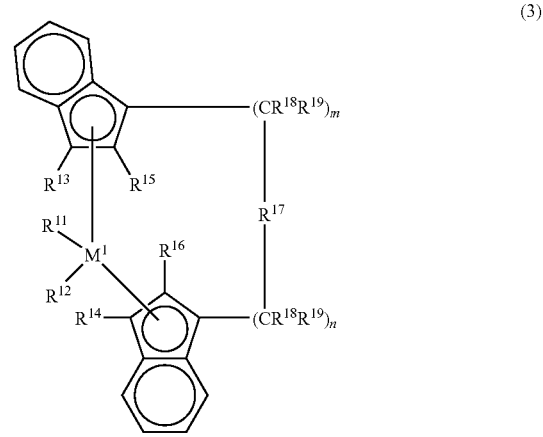

In the formula, $M^1$ is a transition metal of Group 4 of the periodic table, specifically, titanium, zirconium or hafnium. $R^{11}$ and $R^{12}$ are each independently a hydrogen atom, an alkyl group of 1 to 10 carbon atoms, an alkoxy group of 1 to 10 carbon atoms, an aryl group of 6 to 10 carbon atoms, an aryloxy group of 6 to 10 carbon atoms, an alkenyl group of 2 to 10 carbon atoms, an arylalkyl group of 7 to 40 carbon atoms, an alkylaryl group of 7 to 40 carbon atoms, an arylalkenyl group of 8 to 40 carbon atoms or a halogen atom. $R^{11}$ and $R^{12}$ are each preferably a chlorine atom.

In the formula (3), $R^{13}$ and $R^{14}$ are each independently a hydrogen atom, a halogen atom, an alkyl group of 1 to 10 carbon atoms which may be halogenated, an aryl group of 6 to 10 carbon atoms, $-N(R^{20})_2$, $-SR^{20}$, $-OSi(R^{20})_3$, $-Si(R^{20})_3$ or $-P(R^{20})_2$. $R^{20}$ is a halogen atom, preferably a chorine atom; an alkyl group of 1 to 10 carbon atoms, preferably 1 to 3 carbon atoms; or an aryl group of 6 to 10 carbon atoms, preferably 6 to 8 carbon atoms. $R^{13}$ and $R^{14}$ are each particularly preferably a hydrogen atom.

Examples of $R^{15}$ and $R^{16}$ in the formula (3) are the same atoms and groups as defined by $R^{13}$ and $R^{14}$ except a hydrogen atom. Although $R^{15}$ and $R^{16}$ may be the same as or different from each other, they are preferably the same as each other. $R^{15}$ and $R^{16}$ are each preferably an alkyl group of 1 to 4 carbon atoms which may be halogenated, specifically, methyl, ethyl, propyl, isopropyl, butyl, isobutyl or trifluoromethyl, and they are each particularly preferably methyl.

In the formula (3), $R^{17}$ is, for example,

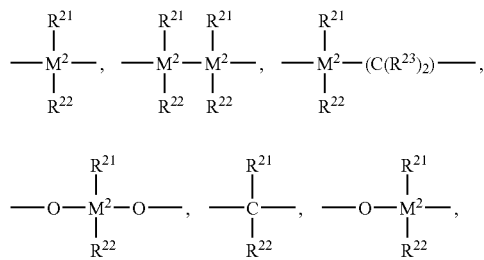

$=BR^{21}$, $=AlR^{21}$, $-Ge-$, $-Sn-$, $-O-$, $-S-$, $=SO$, $=SO_2$, $=NR^{21}$, $=CO$, $=PR^{21}$ or $=P(O)R^{21}$.

$M^2$ is silicon, germanium or tin, preferably silicon or germanium. $R^{21}$, $R^{22}$ and $R^{23}$ are each independently a hydrogen atom, a halogen atom, an alkyl group of 1 to 10 carbon atoms, a fluoroalkyl group of 1 to 10 carbon atoms, an aryl group of 6 to 10 carbon atoms, a fluoroaryl group of 6 to 10 carbon atoms, an alkoxy group of 1 to 10 carbon atoms, an alkenyl group of 2 to 10 carbon atoms, an arylalkyl group of 7 to 40 carbon atoms, an arylalkenyl group of 8 to 40 carbon atoms or an alkylaryl group of 7 to 40 carbon atoms. "$R^{21}$ and $R^{22}$" or "$R^{21}$ and $R^{23}$" may form a ring together with atoms to which they are bonded. $R^{17}$ is preferably $=CR^{21}R^{22}$, $=SiR^{21}R^{22}$, $=GeR^{21}R^{22}$, $-O-$, $-S-$, $=SO$, $=PR^{21}$ or $=P(O)R^{21}$. $R^{18}$ and $R^{19}$ are each independently the same atom or group as exemplified for $R^{21}$. m and n are each independently 0, 1 or 2, preferably 0 or 1. m+n is 0, 1 or 2, preferably 0 or 1.

Examples of the metallocene compounds represented by the formula (3) include rac-ethylene(2-methyl-1-indenyl)-2-zirconium-dichloride and rac-dimethylsilylene(2-methyl-1-indenyl)-2-zirconium-dichloride. These metallocene compounds can be prepared by, for example, a process described in Japanese Patent Laid-Open Publication No. 4-268307/1992.

Example 3 of the Metallocene Compound

As the metallocene compound, a metallocene compound represented by the following formula (4) is also employable.

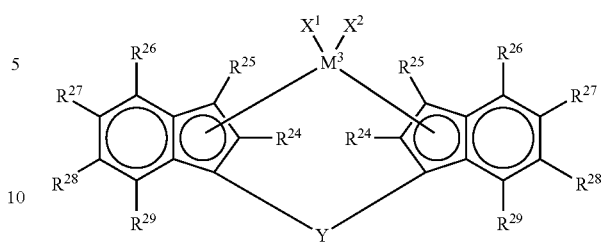

In the formula (4), $M^3$ is a transition metal atom of Group 4 of the periodic table, specifically, titanium, zirconium or hafnium. $R^{24}$ and $R^{25}$ are each independently a hydrogen atom, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group. $R^{24}$ is preferably a hydrocarbon group and is particularly preferably an alkyl group of 1 to 3 carbon atoms, such as methyl, ethyl or propyl. $R^{25}$ is preferably a hydrogen atom or a hydrocarbon group and is particularly preferably a hydrogen atom or an alkyl group of 1 to 3 carbon atoms, such as methyl, ethyl or propyl. $R^{26}$, $R^{27}$, $R^{28}$ and $R^{29}$ are each independently a hydrogen atom, a halogen atom, a hydrocarbon group of 1 to 20 carbon atoms or a halogenated hydrocarbon group of 1 to 20 carbon atoms. Of these, a hydrogen atom, a hydrocarbon group or a halogenated hydrocarbon group is preferable. At least one combination of "$R^{26}$ and $R^{27}$", "$R^{27}$ and $R^{28}$" and "$R^{28}$ and $R^{29}$" may form a monocyclic aromatic ring together with carbon atoms to which they are bonded. When two or more hydrocarbon groups or halogenated hydrocarbon groups are present in addition to the groups which form the aromatic ring, they may be bonded to each other to form a ring. When $R^{29}$ is a substituent other than the aromatic group, it is preferably a hydrogen atom. $X^1$ and $X^2$ are each independently a hydrogen atom, a halogen atom, a hydrocarbon group of 1 to 20 carbon atoms, a halogenated hydrocarbon group of 1 to 20 carbon atoms, an oxygen atom-containing group or a sulfur atom-containing group. Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, $-O-$, $-CO-$, $-S-$, $-SO-$, $-SO_2-$, $-NR^{30}-$, $-P(R^{30})-$, $-P(O)(R^{30})-$, $-BR^{30}-$ or $-AlR^{30}-$. $R^{30}$ is a hydrogen atom, a halogen atom, a hydrocarbon group of 1 to 20 carbon atoms or a halogenated hydrocarbon group of 1 to 20 carbon atoms.

Examples of ligands containing a monocyclic ring that is formed by bonding of at least one combination of "$R^{26}$ and $R^{27}$", "$R^{27}$ and $R^{28}$" and "$R^{28}$ and $R^{29}$" and coordinated to $M^3$ in the formula (4) include those represented by the following formulas:

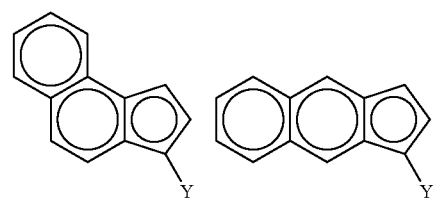

-continued

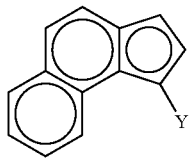

wherein Y has the same definition as that of Y in the formula (4).

Example 4 of the Metallocene Compound

As the metallocene compound, a metallocene compound represented by the following formula (5) is also employable.

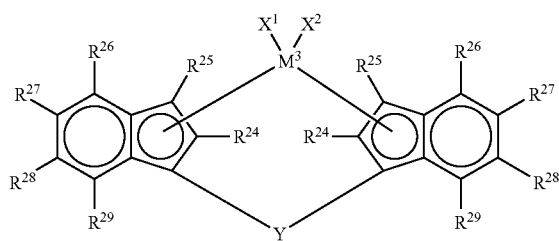

(5)

In the formula (5), $M^3$, $R^{24}$, $R^{25}$, $R^{26}$, $R^{27}$, $R^{28}$ and $R^{29}$ have the same definitions as those in the formula (4). Of $R^{26}$, $R^{27}$, $R^{28}$ and $R^{29}$, two groups including $R^{26}$ are each preferably an alkyl group, and "$R^{26}$ and $R^{28}$" or "$R^{28}$ and $R^{29}$" are preferably alkyl groups. This alkyl group is preferably a secondary or tertiary alkyl group, and may be an alkyl group substituted with a halogen atom or a silicon-containing group. Examples of the halogen atoms and the silicon-containing groups include the substituents previously exemplified for $R^{24}$ and $R^{25}$. Of $R^{26}$, $R^{27}$, $R^{28}$ and $R^{29}$, a group other than an alkyl group is preferably a hydrogen atom. Two groups selected from $R^{26}$, $R^{27}$, $R^{28}$ and $R^{29}$ may be bonded to each other to form a monocyclic or polycyclic ring other than an aromatic ring. Examples of the halogen atoms include the same atoms as described for $R^{24}$ and $R^{25}$. Examples of $X^1$, $X^2$ and Y include the same atoms and groups as previously described.

Examples of the metallocene compounds represented by the formula (5) include rac-dimethylsilylene-bis(4,7-dimethyl-1-indenyl)zirconium dichloride, rac-dimethylsilylene-bis(2,4,7-trimethyl-1-indenyl)zirconium dichloride and rac-dimethylsilylene-bis(2,4,6-trimethyl-1-indenyl)zirconium dichloride.

Transition metal compounds wherein the zirconium metal is replaced with a titanium metal or a hafnium metal in the above compounds are also employable. The transition metal compound is usually used as a racemic modification, but R form or S form is also employable.

Example 5 of the Metallocene Compound

As the metallocene compound, a metallocene compound represented by the following formula (6) is also employable.

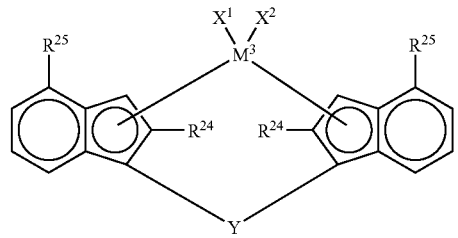

(6)

In the formula (6), $M^3$, $R^{24}$, $X^1$, $X^2$ and Y have the same definitions as those in the formula (4). $R^{24}$ is preferably a hydrocarbon group and is particularly preferably an alkyl group of 1 to 4 carbon atoms, such as methyl, ethyl, propyl or butyl. $R^{25}$ is an aryl group of 6 to 16 carbon atoms. $R^{25}$ is preferably phenyl or naphthyl. The aryl group may be one substituted with a halogen atom, a hydrocarbon group of 1 to 20 carbon atoms or a halogenated hydrocarbon group of 1 to 20 carbon atoms. $X^1$ and $X^2$ are each preferably a halogen atom or a hydrocarbon group of 1 to 20 carbon atoms.

Examples of the metallocene compounds represented by the formula (6) include rac-dimethylsilylene-bis(4-phenyl-1-indenyl)zirconium dichloride, rac-dimethylsilylene-bis(2-methyl-4-phenyl-1-indenyl)zirconium dichloride, rac-dimethylsilylene-bis(2-methyl-4-(α-naphthyl)-1-indenyl)zirconium dichloride, rac-dimethylsilylene-bis(2-methyl-4-(β-naphthyl)-1-indenyl)zirconium dichloride and rac-dimethylsilylene-bis(2-methyl-4-(1-anthryl)-1-indenyl)zirconium dichloride. Transition metal compounds wherein the zirconium metal is replaced with a titanium metal or a hafnium metal in these compounds are also employable.

Example 6 of the Metallocene Compound

As the metallocene compound, a metallocene compound represented by the following formula (7) is also employable.

$$LaM^4X^3{}_2 \qquad (7)$$

In the above formula, $M^4$ is a metal of Group 4 or lanthanum series of the periodic table. La is a derivative of a delocalized n-bond group and is a group that imparts a constrained-geometric shape to the metal $M^4$ active site. Each $X^3$ is independently a hydrogen atom, a halogen atom, a hydrocarbon group of 20 or less carbon atoms, a silyl group containing 20 or less silicon atoms or a germyl group containing 20 or less germanium atoms.

Of such compounds, a compound represented by the following formula (8) is preferable.

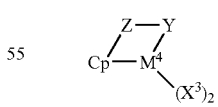

(8)

In the formula (8), $M^4$ is titanium, zirconium or hafnium. $X^3$ has the same definition as that in the formula (7). Cp is a substituted cyclopentadienyl group that is n-bonded to $M^4$ and has a substituent Z. Z is oxygen, sulfur, boron or an element of Group 4 of the periodic table (e.g., silicon, germanium or tin). Y is a ligand containing nitrogen, phosphorus, oxygen or sulfur, and Z and Y may form a condensed ring in cooperation. Examples of the metallocene compounds represented by the formula (8) include (dimethyl(t-butylamido)

(tetramethyl-$\eta^5$-cyclopentadienyl)silane)titanium dichloride and ((t-butylamido)(tetramethyl-$\eta^5$-cyclopentadienyl)-1,2-ethanediyl)titanium dichloride. Transition metal compounds wherein titanium is replaced with zirconium or hafnium in these compounds are also employable.

Example 7 of the Metallocene Compound

As the metallocene compound, a metallocene compound represented by the following formula (9) is also employable.

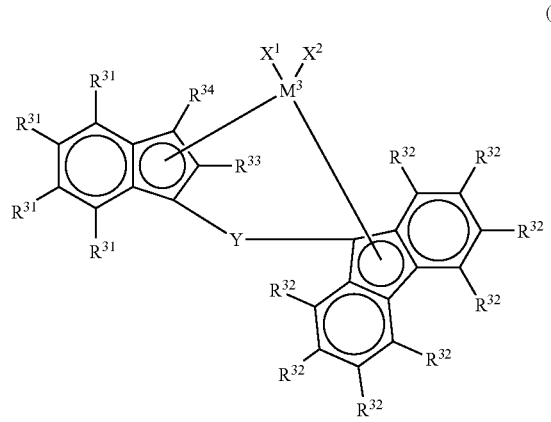

(9)

In the formula (9), $M^3$ is a transition metal atom of Group 4 of the periodic table, specifically, titanium, zirconium or hafnium, preferably zirconium. Plural $R^{31}$ may be the same as or different from one another, and at least one of them is an aryl group of 11 to 20 carbon atoms, an arylalkyl group of 12 to 40 carbon atoms, an arylalkenyl group of 13 to 40 carbon atoms, an alkylaryl group of 12 to 40 carbon atoms or a silicon-containing group, or at least two neighboring groups of the groups indicated by $R^{31}$ form one or plural aromatic rings or aliphatic rings together with carbon atoms to which they are bonded. In this case, the ring formed by $R^{31}$ has 4 to 20 carbon atoms in total including carbon atoms to which $R^{31}$ is bonded. Of plural $R^{31}$, $R^{31}$ other than $R^{31}$ that forms an aryl group, an arylalkyl group, an arylalkenyl group, an alkylaryl group, an aromatic ring or an aliphatic ring is a hydrogen atom, a halogen atom, an alkyl group of 1 to 10 carbon atoms or a silicon-containing group.

Each $R^{32}$ is independently a hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group.

Of the groups indicated by $R^{32}$, at least two neighboring groups may form one or plural aromatic rings or aliphatic rings together with carbon atoms to which they are bonded. In this case, the ring formed by $R^{32}$ has 4 to 20 carbon atoms in total including carbon atoms to which $R^{32}$ is bonded. Of plural $R^{32}$, $R^{32}$ other than $R^{32}$ that forms an aromatic ring or an aliphatic ring is a hydrogen atom, a halogen atom, an alkyl group of 1 to 10 carbon atoms or a silicon-containing group.

The groups, which are constituted by forming one or plural aromatic rings or aliphatic rings from the two groups indicated by $R^{32}$, include a group wherein the fluorenyl group forms the following structure.

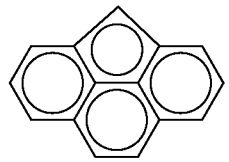

$R^{32}$ is preferably a hydrogen atom or an alkyl group, particularly preferably a hydrogen atom or a hydrocarbon group of 1 to 3 carbon atoms, such as methyl, ethyl or propyl. A preferred example of the fluorenyl group having $R^{32}$ is 2,7-dialkyl-fluoroenyl, and in this case, the alkyl group is, for example, an alkyl group of 1 to 5 carbon atoms. $R^{31}$ and $R^{32}$ may be the same as or different from each other. $R^{33}$ and $R^{34}$ are each independently a hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group. Of these, at least one of $R^{33}$ and $R^{34}$ is preferably an alkyl group of 1 to 3 carbon atoms. $X^1$ and $X^2$ are each independently a hydrogen atom, a halogen atom, an alkyl group of 1 to 20 carbon atoms, a halogenated hydrocarbon group of 1 to 20 carbon atoms, an oxygen-containing group, a sulfur-containing group, a nitrogen-containing group or a conjugated diene residue formed from $X^1$ and $X^2$. Preferred examples of the conjugated diene residues formed from $X^1$ and $X^2$ include residues of 1,3-butadiene, 2,4-hexadiene, 1-phenyl-1,3-pentadiene and 1,4-diphenylbutadiene. These residues may be further substituted with hydrocarbon groups of 1 to 10 carbon atoms. $X^1$ and $X^2$ are each preferably a halogen atom, a hydrocarbon group of 1 to 20 carbon atoms or a sulfur-containing group. Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^{35}$—, —P(R$^{35}$)—, —P(O)(R$^{35}$)—, —BR$^{35}$— or —AlR$^{35}$—. $R^{35}$ is a hydrogen atom, a halogen atom, a hydrocarbon group of 1 to 20 carbon atoms or a halogenated hydrocarbon group of 1 to 20 carbon atoms. Of these divalent groups, groups wherein the shortest connection part of —Y— is constituted of one or two atoms are preferable. $R^{35}$ is preferably a halogen atom, a hydrocarbon group of 1 to 20 carbon atoms or a halogenated hydrocarbon group of 1 to 20 carbon atoms. Y is preferably a divalent hydrocarbon group of 1 to 5 carbon atoms, a divalent silicon-containing group or a divalent germanium-containing group, more preferably a divalent silicon-containing group, particularly preferably alkylsilylene, alkylarylsilylene or arylsilylene.

Example 8 of the Metallocene Compound

As the metallocene compound, a metallocene compound represented by the following formula (10) is also employable.

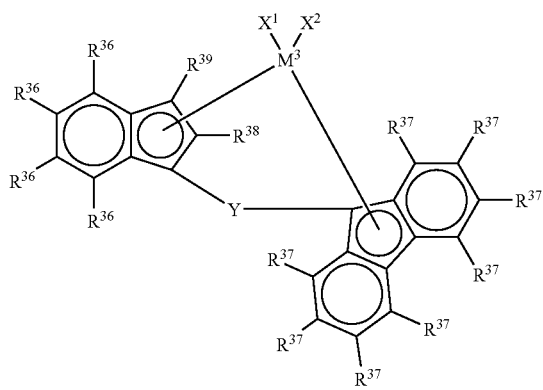

(10)

In the formula (10), $M^3$ is a transition metal atom of Group 4 of the periodic table, specifically, titanium, zirconium or hafnium, preferably zirconium. Each $R^{36}$ is independently a hydrogen atom, a halogen atom, an alkyl group of 1 to 10 carbon atoms, an aryl group of 6 to 10 carbon atoms, an alkenyl group of 2 to 10 carbon atoms, a silicon-containing group, an oxygen-containing group, a sulfur-containing group, a nitrogen-containing group or a phosphorus-containing group. The alkyl group and the alkenyl group may be substituted with halogen atoms. Of these, $R^{36}$ is preferably an alkyl group, an aryl group or a hydrogen atom, particularly preferably a hydrocarbon group of 1 to 3 carbon atoms, such as methyl, ethyl, n-propyl or i-propyl, an aryl group, such as phenyl, α-naphthyl or β-naphthyl, or a hydrogen atom. Each $R^{37}$ is independently a hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group. The alkyl group, the aryl group, the alkenyl group, the arylalkyl group, the arylalkenyl group and the alkylaryl group may be substituted with halogen atoms. $R^{37}$ is preferably a hydrogen atom or an alkyl group, particularly preferably a hydrogen atom or a hydrocarbon group of 1 to 4 carbon atoms, such as methyl, ethyl, n-propyl, i-propyl, n-butyl or tert-butyl. $R^{36}$ and $R^{37}$ may be the same as or different from each other. One of $R^{38}$ and $R^{39}$ is an alkyl group of 1 to 5 carbon atoms, and the other is a hydrogen atom, a halogen atom, an alkyl group of 1 to 10 carbon atoms, an alkenyl group of 2 to 10 carbon atoms, a silicon-containing group, an oxygen-containing group, a sulfur-containing group, a nitrogen-containing group or a phosphorus-containing group. One of $R^{38}$ and $R^{39}$ is preferably an alkyl group of 1 to 3 carbon atoms, such as methyl, ethyl or propyl, and the other is preferably a hydrogen atom. $X^1$ and $X^2$ are each independently a hydrogen atom, a halogen atom, an hydrocarbon group of 1 to 20 carbon atoms, a halogenated hydrocarbon group of 1 to 20 carbon atoms, an oxygen-containing group, a sulfur-containing group, a nitrogen-containing group or a conjugated diene residue formed from $X^1$ and $X^2$. Of these, a halogen atom or a hydrocarbon group of 1 to 20 carbon atoms is preferable. Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^{40}$—, —P(R$^{40}$)—, —P(O)(R$^{40}$)—, —BR$^{40}$— or —AlR$^{40}$—. $R^{40}$ is a hydrogen atom, a halogen atom, a hydrocarbon group of 1 to 20 carbon atoms or a halogenated hydrocarbon group of 1 to 20 carbon atoms. Y is preferably a divalent hydrocarbon group of 1 to 5 carbon atoms, a divalent silicon-containing group or a divalent germanium-containing group, more preferably a divalent silicon-containing group, particularly preferably alkylsilylene, alkylarylsilylene or arylsilylene.

The metallocene compounds mentioned above are used singly or in combination of two or more kinds. The metallocene compounds may be used after diluted with hydrocarbon, halogenated hydrocarbon or the like.

(Organoaluminum Oxy-Compound)

The organoaluminum oxy-compound may be publicly known aluminoxane, or may be a benzene-insoluble organoaluminum oxy-compound. The publicly known aluminoxane is specifically represented by the following formula.

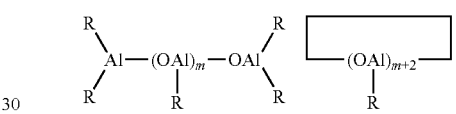

In the above formulas, R is a hydrocarbon group, such as methyl, ethyl, propyl or butyl, preferably methyl or ethyl, particularly preferably methyl, and m is an integer of 2 or more, preferably an integer of 5 to 40.

The aluminoxane may comprise mixed alkyloxyaluminum units consisting of an alkyloxyaluminum unit represented by the formula —(OAl(R'))— and an alkyloxyaluminum unit represented by the formula —(OAl(R''))—. Examples of R' and R'' include the same hydrocarbon groups as previously described for R, and R' and R'' are groups different from each other. The organoaluminum oxy-compound may contain a small amount of an organic compound component of a metal other than aluminum.

(Ionizing Ionic Compound)

The ionizing ionic compound (sometimes referred to as "ionic ionizing compound" or "ionic compound") is, for example, a Lewis acid, an ionic compound, a borane compound or a carborane compound. The Lewis acid is, for example, a compound represented by BR$_3$ (R is fluorine or a phenyl group which may have a substituent, such as fluorine, methyl or trifluoromethyl). Examples of the Lewis acids include trifluoroboron, triphenylboron, tris(4-fluorophenyl) boron, tris(3,5-difluorophenyl)boron, tris(4-fluoromethylphenyl)boron, tris(pentafluorophenyl)boron, tris(p-tolyl) boron, tris(o-tolyl)boron and tris(3,5-dimethylphenyl)boron.

Examples of the ionic compounds include trialkyl-substituted ammonium salts, N,N-dialkylanilinium salts, dialkylammonium salts and triarylphosphonium salts. Examples of the trialkyl-substituted ammonium salts as the ionic compounds include triethylammonium tetra(phenyl)boron, tripropylammonium tetra(phenyl)boron and tri(n-butyl)ammonium tetra(phenyl)boron. Examples of the dialkylammonium salts as the ionic compounds include di(1-propyl)ammonium tetra(pentafluorophenyl)boron and dicyclohexylammonium tetra(phenyl)boron.

As the ionic compounds, triphenylcarbenium tetrakis(pentafluorophenyl)borate, N,N-dimethylanilinium tetrakis(pentafluorophenyl)borate and ferrocenium tetra(pentafluorophenyl)borate can be also exemplified.

Examples of the borane compounds include decaborane (9), bis[tri(n-butyl)ammonium]nonaborate, bis[tri(n-butyl)ammonium]decaborate, and salts of metallic borane anions, such as bis[tri(n-butyl)ammonium]bis(dodecahydrododecaborato)nickelate(III).

Examples of the carborane compounds include 4-carbanonaborane(9), 1,3-dicarbanonaborane(8), and salts of metallic carborane anions, such as bis[tri(n-butyl)ammonium]bis(undecahydrido-7-carbaundecaborato)nickelate (IV).

The ionizing ionic compounds are used singly or in combination of two or more kinds.

In the preparation of the metallocene catalyst, the following organoaluminum compound may be used together with the oraganoaluminum oxy-compound and/or the ionizing ionic compound.
(Organoaluminum Compound)

As the organoaluminum compound that is used when needed, a compound having at least one Al-carbon bond in the molecule is employable. The compound is, for example, an organoaluminum compound represented by the following formula (11) or an alkyl complex compound of a Group 1 metal and aluminum, which is represented by the following formula (12).

$$(R^6)_m Al(OR^7)_n H_p X^4_q \quad (11)$$

wherein $R^6$ and $R^7$ are each independently a hydrocarbon group containing usually 1 to 15 carbon atoms, preferably 1 to 4 carbon atoms, $X^4$ is a halogen atom, and m, n, p and q are numbers satisfying the conditions of $0<m\leq3$, $0\leq n<3$, $0\leq p<3$, $0\leq q<3$ and $m+n+p+q=3$.

$$(M^5)Al(R^6) \quad (12)$$

wherein $M^5$ is Li, Na or K, and $R^6$ has the same definition as that of $R^6$ in the formula (11).
(Polymerization)

The olefin wax (A) of the invention is obtained by copolymerizing ethylene and a diene usually in a liquid phase or copolymerizing ethylene, at least one α-olefin selected from α-olefins of 3 to 12 carbon atoms and at least one diene, in the presence of the above-mentioned metallocene catalyst. In the polymerization, a hydrocarbon solvent is generally used, but an α-olefin may be used as a solvent. The monomers used herein are as previously described.

As the polymerization process, suspension polymerization wherein polymerization is carried out in such a state that the olefin wax (A) is present in the form of particles in a solvent such as hexane, vapor phase polymerization wherein polymerization is carried out without a solvent, or solution polymerization wherein polymerization is carried out in such a state that the olefin wax (A) is present together with a solvent or is molten alone is available. Of these, solution polymerization is preferable in both respects of economical efficiency and quality.

The polymerization reaction may be carried out batchwise or continuously. When the polymerization is carried out batchwise, the catalyst components are used under the following concentration conditions.

The concentration of the metallocene compound in the polymerization system is in the range of usually 0.00005 to 0.1 mmol/liter (polymerization volume), preferably 0.0001 to 0.05 mmol/liter.

The organoaluminum oxy-compound is fed in such an amount that the molar ratio (Al/transition metal) of the aluminum atom to the transition metal in the metallocene compound in the polymerization system becomes 1 to 10000, preferably 10 to 5000.

The ionizing ionic compound is fed in such an amount that the molar ratio (ionizing ionic compound/metallocene compound) of the ionizing ionic compound to the metallocene compound in the polymerization system becomes 0.5 to 20, preferably 1 to 10.

When the organoaluminum compound is used, the organoaluminum compound is used in an amount of usually about 0 to 5 mmol/liter (polymerization volume), preferably about 0 to 2 mmol/liter.

The polymerization reaction is carried out under the conditions of a temperature of usually −20 to +200° C., preferably 50 to 180° C., more preferably 70 to 180° C., and a pressure of exceeding 0 and not more than 7.8 MPa (80 kgf/cm², gauge pressure), preferably exceeding 0 and not more than 4.9 MPa (50 kgf/cm², gauge pressure).

In the polymerization, ethylene, at least one diene and at least one α-olefin selected from α-olefins of 3 to 20 carbon atoms, said α-olefin being used when needed, are fed to the polymerization system in such amounts that the olefin wax (A) of the aforesaid specific composition is obtained. In the polymerization, a molecular weight modifier such as hydrogen can be added.

By carrying out the polymerization in the above manner, the resultant polymer can be usually obtained as a polymer solution containing it, and hence, the polymer solution is treated in a conventional manner to give the olefin wax (A).

In the polymerization reaction, it is particularly preferable to use a catalyst containing the metallocene compound described in the example 6 of the metallocene compound.

Silicone-Modified Olefin Wax

The silicone modified olefin wax (B) of the invention is one obtained by hydrosilylating the olefin wax (A) with hydrogen silicone.

As the silicone subjected to the reaction, any hydrogen silicone known in the prior art may be used, but preferable is hydrogen silicone having one or more hydrosilyl group (SiH bond) in one molecule. Although hydrogen silicone having a hydrosilyl group in the side chain of silicone is preferable, hydrogen silicone having a hydrosilyl group at both terminals or one terminal is also employable. From the viewpoint of cost, hydrogen silicone having a hydrosilyl group in only the side chain of silicone is most advantageous. The reaction of the olefin wax (A) with hydrogen silicone is carried out using a platinum catalyst in a solvent or without a solvent, as publicly known. The reaction temperature is in the range of 30 to 200° C., particularly preferably 120 to 150° C. Since the olefin wax (A) has a melting point of about 120° C., the reaction temperature is preferably set at not lower than 120° C. from the viewpoint of homogeneity of the reaction system. The reaction of hydrogen silicone with the olefin wax (A) is carried out under such conditions that the amount of the olefin wax (A) becomes in small excess, specifically, about 1.05 to 1.2 times by mol the amount of the hydrogen silicone, without limiting thereto. More specifically, the reaction is carried out in the presence of a high-boiling point solvent such as xylene, and the solvent is distilled off under reduced pressure, whereby a silicone-modified olefin wax (B) can be obtained.

As the hydrogen silicone, a silane or siloxane compound having two or more hydrolyzable groups in one molecule may be used. Examples of the hydrolyzable groups include alkoxy groups, such as methoxy, ethoxy and butoxy; ketoxime groups, such as dimethylketoxime and methylethylketoxime; acyloxy groups, such as acetoxy; alkenyloxy groups, such as isopropenyloxy and isobutenyloxy; amino groups, such as N-butylamino and N,N-diethylamino; and amido groups, such as N-methylacetamido. Of these, alkoxy groups, ketoxime groups, alkenyloxy groups and acyloxy groups are preferable.

The olefin wax (A) and the silicone-modified olefin wax (B) can be used in combination with a silane coupling agent. As the silane coupling agent, any of silane coupling agents known in the prior art may be employed. A typical silane coupling agent is, for example, an acrylic (methacrylic) functional silane coupling agent, an epoxy functional silane coupling agent or an amino (imino) functional silane coupling agent.

Examples of the acrylic (methacrylic) functional silane coupling agents include 3-methacryloxypropyltrimethoxysilane, 3-methacryloxypropyltriethoxysilane, 3-acryloxypropyltrimethoxysilane, 3-acryloxypropyltriethoxysilane, methacryloxymethyltrimethoxysilane, methacryloxymethyltriethoxysilane, acryloxymethyltrimethoxysilane and acryloxymethyltriethoxysilane.

Examples of the epoxy functional silane coupling agents include 3-glycidoxypropyltrimethoxysilane, 3-glycidoxypropyltriethoxysilane, 2-(3,4-epoxycyclohexyl)ethyltrimethoxysilane and 2-(3,4-epoxycyclohexyl)ethyltriethoxysilane.

Examples of the amino (imino) functional silane coupling agents include amino group- and/or imino group-containing alkoxysilanes, such as $H_2NCH_2CH_2CH_2Si(OCH_3)_3$, $H_2NCH_2CH_2NHCH_2CH_2CH_2Si(OCH_3)_3$, $H_2NCH_2CH_2NHCH_2CH_2CH_2Si(CH_3)(OCH_3)_2$ and $(C_2H_5O)_3Si(CH_2)_3NH(CH_2)_2NH(CH_2)_3Si(OC_2H_5)_3$; reaction products of amino group- and/or imino group-containing alkoxysilanes with epoxysilane compounds; and reaction products of amino group- and/or imino group-containing alkoxysilanes with methacryloxysilane compounds such as $CH_2=C(CH_3)COOCH_2CH_2CH_2Si(OCH_3)_3$ and $CH_2=C(CH_3)COOCH_2CH_2CH_2Si(OCH_2CH_2OCH_3)_3$.

Silicone-Modified Room Temperature-Solidifying Composition

The silicone-modified room temperature-solidifying composition (D) of the invention contains the above silicone-modified olefin wax (B), and comprises, for example, the silicone-modified olefin wax (B) and the later-described oil agent (C).

The silicone-modified room temperature-solidifying composition (D) of the invention preferably contains the silicone-modified olefin wax (B) in an amount of 5 to 95% by mass. When the silicone-modified room temperature-solidifying composition (D) comprises the silicone-modified olefin wax (B) and the oil agent (C), it is desirable that the silicone-modified olefin wax (B) is contained in an amount of 5 to 95% by mass, preferably 20 to 80% by mass, more preferably 30 to 70% by mass, and the oil agent (C) is contained in an amount of 95 to 5% by mass, preferably 80 to 20% by mass, more preferably 70 to 30% by mass.

When the content of each component is in the above range, the silicone-modified room temperature-solidifying composition (D) having moderate hardness can be obtained.

The silicone-modified room temperature-solidifying composition (D) of the invention can be used not only for the below-described cosmetic but also for toner internal additives, car waxes, and various release agents.

Cosmetic

The cosmetic of the invention contains the silicone-modified olefin wax (B) and/or the silicone-modified room temperature-solidifying composition (D). In more detail, the cosmetic contains the silicone-modified olefin wax (B), and if necessary, the oil agent (C).

Examples of the cosmetics of the invention include skin care cosmetics, such as lotion, emulsion, cream, cleanser, face pack, oil liquid, cosmetic for massage, detergent, deodorant, hand cream and lip cream; make-up cosmetics; such as make-up foundation, face powder, liquid foundation, oil foundation, cheek rouge, eye shadow, mascara, eye liner, cosmetic for eyebrow and lipstick; hair cosmetics, such as shampoo, conditioner, hair treatment and hair styling product; antiperspirant cosmetics; and ultraviolet protective cosmetics, such as anti-suntan emulsion and anti-suntan cream.

The cosmetic of the invention may take various forms, such as liquid, emulsion, cream, solid, paste, gel, powder, pressed, multi-layer, mousse, spray, stick and pencil forms. In particular, solid or stick form is preferable.

(C) Oil Agent

The silicone-modified room temperature-solidifying composition (D) and the cosmetic of the invention can contain one or more oil agents (C) according to the purpose. As the oil agent (C), any of oil agents which are solid, semisolid or liquid at room temperature is employable provided that it is used for usual cosmetics.

Examples of natural animal and plant fats and oils and semisynthetic resins include avocado oil, linseed oil, almond oil, insect wax, perilla oil, olive oil, cacao butter, kapok wax, Japanese nutmeg oil, carnauba wax, liver oil, candelilla wax, beef tallow, neat's-foot oil, beef bone fat, hydrogenated beef tallow, apricot kernel oil, spermaceti, hydrogenated oil, wheat germ oil, sesame oil, rice germ oil, rice bran oil, sugarcane wax, sasanqua oil, safflower oil, shea butter, Chinese wood oil, cinnamon oil, jojoba wax, shellac wax, turtle oil, soybean oil, tea seed oil, camellia oil, evening primrose oil, corn oil, lard, rape seed oil, Japanese wood oil, bran wax, germ oil, horse tallow, persic oil, palm oil, palm kernel oil, castor oil, hydrogenated castor oil, castor oil fatty acid methyl ester, sunflower oil, grape seed oil, bayberry wax, jojoba oil, macadamia nut oil, beeswax, mink oil, cottonseed oil, cotton wax, Japan wax, Japan wax kernel oil, montan wax, fractionated coconut oil, hydrogenated fractionated-coconut oil, coconut fatty acid triglyceride, mutton tallow, peanut oil, lanolin, liquid lanolin, reduced lanolin, lanolin alcohol, hard lanolin, lanolin acetate, lanolin fatty acid isopropyl ester, hexyl laurate, POE lanolin alcohol ether, POE lanolin alcohol acetate, lanolin fatty acid polyethylene glycol, POE hydrogenated lanolin alcohol ether, and egg yolk oil. The term "POE" used herein means polyoxyethylene.

Examples of hydrocarbon oils include ozokerite, squalane, squalene, ceresin, paraffin, paraffin wax, liquid paraffin, pristane, polyisobutylene, microcrystalline wax and vaseline.

Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, POE cholesterol ether, monostearyl glyceryl ether(batyl alcohol) and monooleyl glyceryl ether(selachyl alcohol).

Examples of ester oils include diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate and di isostearyl malate. Examples of glyceride oils include acetoglyceryl, glyceryl triisooctanoate, glyceryl triisostearate, glyceryl triisopalmitate, glyceryl monostearate, glyceryl di-2-heptylundecanoate, glyceryl trimyristate and diglyceryl myristate isostearate.

Examples of silicone oils include organopolysiloxanes of low-viscosity to high-viscosity, such as dimethylpolysiloxane, methylphenylpolysiloxane, methylhydrogenpolysiloxane and dimethylsiloxane/methylphenylsiloxane copolymer; cyclic siloxanes, such as octamethylcyclotetrasiloxane, decamethylcyclopentasiloxane, dodecamethylcyclohexasiloxane, tetramethyltetrahydrogencyclotetrasiloxane and tetramethyltetraphenylcyclotetrasiloxane; silicone rubbers, such as highly polymerized gum dimethylpolysiloxane and gum dimethylsiloxane/methylphenylsiloxane copolymer, and cyclic siloxane solutions of the silicone rubbers; trimethylsiloxysilicic acid, and cyclic siloxane solution of trimethylsiloxysilicic acid; higher alkoxy-modified silicones, such as stearoxy silicone; higher fatty acid-modified silicones; alkyl-modified silicones; amino-modified silicones; fluorine-modified silicones; and dissolution products of silicone resins.

The structure of the silicone. oil is not specifically restricted, and it may be any of linear, branched and cyclic. In particular, a structure most of which comprises —[Si—O—]$_n$— skeleton is preferable. Such a silicone oil may have a —Si—(CH$_2$CH$_2$)$_m$—Si— bond as a part of a molecule.

The silicone oil may be a linear, branched or cyclic silicone oil represented by the following formula:

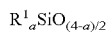

wherein $R^1$ is a hydrogen atom, an alkyl group or a fluorine-substituted alkyl group of 1 to 30 carbon atoms, an aryl group of 6 to 30 carbon atoms or an aralkyl group of 7 to 30 carbon atoms, and a is a number satisfying the condition of $0 \leq a \leq 2.5$.

A part of the oil agent (C) for use in the invention is preferably a silicone oil represented by the above formula.

A part of the oil agent (C) for use in the invention may have a fluorine atom or an amino group. The fluorinated oil agent is, for example, perfluoropolyether, perfluorodecalin or perfluorooctane.

A part of the oil agent (C) for use in the invention is preferably liquid at room temperature, and is also preferably a solid oil agent having a melting point of not lower than 50° C.

When the oil agent (C) is added to the cosmetic, the amount thereof is in the range of preferably 1 to 98% by mass. Especially when the cosmetic is in the form of a solid or a stick, the amount of the oil agent added is preferably in the range of 5 to 95% by mass based on the total amount of the cosmetic.

To the silicone-modified room temperature-solidifying composition (D) and the cosmetic of the invention, the following components may be added in addition to the silicone-modified olefin wax (B) and the oil agent (C) according to the purpose.

(E) Water

To the silicone-modified room temperature-solidifying composition (D) and the cosmetic of the invention, water (E) can be added according to the purpose. The amount of water (E) added is in the range of preferably 1 to 95% by mass based on the total amount of the cosmetic.

(F) Compound Having Alcoholic Hydroxyl Group in Molecular Structure

In the silicone-modified room temperature-solidifying composition (D) and the cosmetic of the invention, a compound (F) having an alcoholic hydroxyl group in the molecular structure can be used singly or in combination of two or more kinds, according to the purpose.

Examples of the compounds (F) having an alcoholic hydroxyl group in the molecular structure include lower alcohols, such as ethanol and isopropanol; sugar alcohols, such as sorbitol and maltose; sterols, such as cholesterol, sitosterol, phytosterol and lanosterol; and polyhydric alcohols, such as butylene glycol, propylene glycol and dibutylene glycol. The amount of the compound (F) having an alcoholic hydroxyl group in the molecular structure is in the range of preferably 0.1 to 98% by mass based on the total amount of the cosmetic.

(G) Water-Soluble or Water-Swelling High-Molecular Substance

In the silicone-modified room temperature-solidifying composition (D) and the cosmetic of the invention, a water-soluble or water-swelling high-molecular substance (G) can be used singly or in combination of two or more kinds, according to the purpose.

Examples of the water-soluble or water-swelling high-molecular substances (G) include plant-derived high-molecular substances, such as gum arabic, tragacanth, galactan, carob gum, guar gum, karaya gum, carrageenan, pectin, agar, quince seed (marmelo), starch (rice, corn, potato, wheat), Algaecolloid, tragacanth gum and locust bean gum; microorganism-derived high-molecular substances, such as xanthan gum, dextran, succinoglucan and pullulan; animal-derived high-molecular substances, such as collagen, casein, albumin and gelatin; starch-based high-molecular substances, such as carboxymethyl starch and methylhydroxypropyl starch; cellulose-based high-molecular substances, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystal cellulose and cellulose powder; alginic acid-based high-molecular substances, such as sodium alginate and propylene glycol alginate; vinyl high-molecular substances, such as polyvinyl methyl ether and carboxyvinyl polymer; polyoxyethylene-based high-molecular substances; polyoxyethylene/polyoxypropylene copolymer-based high-molecular substances; acrylic high-molecular substances, such as sodium polyacrylate, polyethyl acrylate and polyacrylamide; other synthetic water-soluble high-molecular substances, such as polyethyleneimine and cation polymer; and inorganic water-soluble high-molecular substances, such as bentonite, magnesium aluminum silicate, montmorillonite, beidellite, nontronite, saponite, hectorite and silicic acid anhydride. These water-soluble high-molecular substances also include film-forming agents, such as polyvinyl alcohol and polyvinyl pyrrolidone.

The amount of the water-soluble or water-swelling high-molecular substance (G) added is in the range of preferably 0.1 to 25% by mass based on the total amount of the cosmetic.

(H) Powder and/or Colorant

In the silicone-modified room temperature-solidifying composition (D) and the cosmetic of the invention, a powder (H1) and/or a colorant (H2) can be used singly or in combination of two or more kinds, according to the purpose.

As the powder (H1) and the colorant (H2), any of powders and colorants which are used for usual cosmetics are employable irrespective of their shapes (spherical, acicular, plate-like, etc.), particle diameters (spray size, fine particle size, pigment size, etc.) and particle structures (porous, non-porous, etc.). For example, inorganic powders, organic powders, metallic salt powders of surface active agent, color pigments, pearl pigments, metallic powder pigments and natural dyes are available.

Examples of the inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic acid anhydride, aluminum silicate, magnesium silicate, magnesium aluminum silicate, calcium silicate, barium silicate, strontium silicate, tungstic acid metallic salt, hydroxyapatite, vermiculite, HYGILITE (trade name), bentonite, montmorillonite, hectorite, zeolite, ceramic powder, dibasic calcium phosphate, alumina, aluminum hydroxide, boron nitride and silica.

Examples of the organic powders include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, cellulose, silk powder, nylon powder, 12-nylon, 6-nylon, crosslinked silicone fine powder having a structure wherein dimethyl silicone is crosslinked, polymethylsilsesquioxane fine powder, styrene/acrylic acid copolymer, divinylbenzene/styrene copolymer, vinyl resin, urea resin, phenolic resin, fluorocarbon resin, silicon resin, acrylic resin, melamine resin, epoxy resin, polycarbonate resin, fine crystal fiber powder, starch powder and lauroyl lysine. An organic powder most of which is formed from —[Si—O—]$_n$— skeleton is also employable. This organic powder may have a —Si—(CH$_2$CH$_2$)$_n$—Si— bond as a part of a molecule.

Examples of the metallic salt powders of the surface active agent (metallic soaps) include zinc stearate, aluminum stearate, calcium stearate, magnesium stearate, zinc myristate, magnesium myristate, zinc cetyl phosphate, calcium cetyl phosphate and sodium zinc cetyl phosphate.

Examples of the color pigments include inorganic red pigments, such as iron oxide, iron hydroxide and iron titanate; inorganic brown pigments, such as γ-iron oxide; inorganic yellow pigments, such as yellow iron oxide and yellow ocher; inorganic black pigments, such as black iron oxide and carbon black; inorganic violet pigments, such as manganese violet and cobalt violet; inorganic green pigments, such as chromium hydroxide, chromium oxide, cobalt oxide and cobalt titanate; inorganic blue pigments, such as prussian blue and ultramarine blue; lakes formed from tar dyes; lakes formed from natural dyes; and synthetic resin powders which are composites of these powders.

Examples of the pearl pigments include titanium oxide-coated mica, bismuth oxychloride, titanium oxide-coated bismuth oxychloride, titanium oxide-coated talc, argentine and titanium oxide-coated colored mica.

Examples of the metallic powder pigments include aluminum powder, copper powder and stainless steel powder.

Examples of the tar dyes include red No. 3, red No. 104, red No. 106, red No. 201, red No. 202, red No. 204, red No. 205, red No. 220, red No. 226, red No. 227, red No. 228, red No. 230, red No. 401, red No. 505, yellow No. 4, yellow No. 5, yellow No. 202, yellow No. 203, yellow No. 204, yellow No. 401, blue No. 1, blue No. 2, blue No. 201, blue No. 404, green No. 3, green No. 201, green No. 204, green No. 205, orange No. 201, orange No. 203, orange No. 204, orange No. 206 and orange No. 207.

Examples of the natural dyes include powders selected from carminic acid, laccaic acid, carthamine, brazilin and crocin. Further, composites of these powders; powders given by treating these powders with general oil agents, silicone oils, fluorine compounds, surface active agents or the like; reactive organohydrogenpolysiloxane, organopolysiloxane having hydrolyzable alkoxysilane group, and acryl/silicone copolymers having hydrolyzable silyl group are also employable, within limits not detrimental to the effects of the present invention. They can be used singly or in combination of two or more kinds according to necessity.

A part of the powder (H1) and/or the colorant (H2) is preferably a crosslinked spherical dimethylpolysiloxane fine powder having a structure wherein dimethylpolysiloxane is crosslinked, a crosslinked spherical polymethylsilsesquioxane fine powder, hydrophobic silica or a fine powder obtained by coating a surface of a crosslinked spherical polysiloxane rubber with polymethylsilsesquioxane particles. Further, a part of the powder (H1) and/or the colorant (H2) also preferably has a fluorine atom.

The amount of the powder (H1) and/or the colorant (H2) added is in the range of preferably 0.1 to 99% by mass based on the total amount of the cosmetic. Especially when the cosmetic is a powder solid cosmetic, the amount of the powder (H1) and/or the colorant (H2) is in the range of preferably 80 to 90% by mass based on the total amount of the cosmetic.

(I) Surface Active Agent

In the silicone-modified room temperature-solidifying composition (D) and the cosmetic of the invention, a surface active agent (I) can be used singly or in combination of two or more kinds, according to the purpose. Examples of the surface active agents (I) include anionic, cationic, nonionic and amphoteric surface active agents. In the present invention, there is no specific limitation on the surface active agent (I) used, and any of surface active agents which are used for usual cosmetics is employable.

Examples of the anionic surface active agents include fatty acid soaps, such as sodium stearate and triethanolamine palmitate; alkyl ether carboxylic acid and a salt thereof; condensate salt of amino acid and fatty acid; alkanesulfonate; alkenesulfonate; sulfonate of fatty acid ester; sulfonate of fatty acid amide; formalin condensate-based sulfonate; sulfuric ester salts, such as alkylsulfuric ester salt, secondary higher alcohol sulfuric ester salt, alkyl and allyl ether sulfuric ester salt, sulfuric ester salt of fatty acid ester, sulfuric ester salt of fatty acid alkylolamide and Turkey red oil; alkylphosphate; ether phosphate; alkylallyl ether phosphate; amidophosphate; and N-acylamino acid-based active agent.

Examples of the cationic surface active agents include amine salts, such as alkylamine salt, polyamine and amino alcohol fatty acid derivative; alkyl quaternary ammonium salt, aromatic quaternary ammonium salt, pyridinium salt and imidazolium salt.

Examples of the nonionic surface active agents include sorbitan fatty acid ester, glycerine fatty acid ester, polyglycerine fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkylphenyl ether, polyoxyethylene fatty acid ester, polyoxyethylene sorbitan fatty acid ester, polyoxyethylene sorbitol fatty acid ester, polyoxyethylene glycerine fatty acid ester, polyoxyethylene propylene glycol fatty acid ester, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, alkanol amide, sugar ether and sugar amide. Linear or branched silicone having a polyoxyalkylene chain in the molecule, such as linear or branched and polyoxyalkylene-modified organopolysiloxane or linear or branched and polyoxyalkylene/alkyl-comodified organopolysiloxane, and linear or branched silicone having a polyglycerin chain in the molecule, such as linear or branched and polyglycerin-modified organopolysiloxnane or linear or branched and polyglycerin/alkyl-comodified organopolysiloxane, are also employable.

Examples of the amphoteric surface active agents include betaine, aminocarboxylate, imidazoline derivative and amidoamine-based surface active agent.

The surface active agent (I) for use in the invention preferably has a hydrophilic-lipophilic balance (HLB) of 2 to 8.

The amount of the surface active agent (I) added is desired to be in the range of 0.1 to 20% by mass, particularly preferably 0.2 to 10% by mass, based on the total amount of the cosmetic.

(J) Crosslinkable Organopolysiloxane

In the silicone-modified room temperature-solidifying composition (D) and the cosmetic of the invention, crosslinkable organopolysiloxane (J) can be used singly or in combination of two or more kinds, according to the purpose.

The crosslinkable organopolysiloxane (J) preferably contains low-viscosity silicone having a viscosity of 0.65 to 10.0 $mm^2$/sec (25° C.) and preferably swells. The content of the low-viscosity silicone is preferably not less than the weight of the crosslinkable organopolysiloxane (J) itself. The crosslinkable organopolysiloxane (J) preferably forms a crosslinked structure by the reaction of a hydrogen atom directly bonded to a silicon atom in the molecule of the organopolysiloxane (J) with a crosslinking agent having two or more vinyl reaction sites in the molecule. The crosslinkable organopolysiloxane (J) preferably contains at least one site selected from the group consisting of polyoxyalkylene, polyglycerin, alkyl, alkenyl, aryl and fluoroalkyl in a crosslinkable molecule.

The amount of the crosslinkable organopolysiloxane (J) added is desired to be in the range of preferably 0.1 to 30.0% by mass, more preferably 1.0 to 10.0% by mass, based on the total amount of the silicone-modified room temperature-solidifying composition (D). When the crosslinkable organopolysiloxane (J) is added to the cosmetic, the amount thereof is desired to be in the range of preferably 0.1 to 50% by mass, particularly preferably 0.5 to 30% by mass, based on the total amount of the cosmetic.

(K) Silicone Resin

In the silicone-modified room temperature-solidifying composition (D) and the cosmetic of the invention, a silicone resin (K) can be used singly or in combination of two or more kinds, according to the purpose.

The silicone resin (K) is preferably an acrylic silicone resin comprising a graft or block copolymer of acryl/silicone. An acrylic silicone resin containing at least one site selected from the group consisting of pyrrolidone, long-chain alkyl, polyoxyalkylene, fluoroalkyl and anions of carboxylic acids or the like in a molecule is also employable.

The silicone resin (K) is preferably a silicone network compound selected from a silicone network compound (MQ) consisting essentially of a monofunctional siloxy group and a tetrafunctional siloxy group; a silicone network compound (MDQ) consisting essentially of a monofunctional siloxy group, a bifunctional siloxy group and a tetrafunctional siloxy group; a silicone network compound (MT) consisting essentially of a monofunctional siloxy group and a trifunctional siloxy group; a silicone network compound (MDT) consisting essentially of a monofunctional siloxy group, a bifunctional siloxy group and a trifunctional siloxy group; and a silicone network compound (MDTQ) consisting essentially of a monofunctional siloxy group, a bifunctional siloxy group, a trifunctional siloxy group and a tetrafunctional siloxy group.

As the silicone resin (K), a silicone network compound containing at least one site selected from the group consisting of pyrrolidone, long-chain alkyl, polyoxyalkylene, fluoroalkyl and an amino group in the molecule is also employable.

Of the above silicone resins, the acrylic silicone resin is particularly preferable for the silicone-modified room temperature-solidifying composition (D) of the invention.

The amount of the silicone resin (K) added is desired to be in the range of preferably 0.1 to 20% by mass, more preferably 1 to 10% by mass, based on the total amount of the silicone-modified room temperature-solidifying composition (D). When the silicone resin (K) is added to the cosmetic, the amount thereof is desired to be in the range of preferably 0.1 to 20% by mass, particularly preferably 1 to 10% by mass, based on the total amount of the cosmetic.

A solution obtained by dissolving a silicone resin such as a graft or block copolymer of acryl/silicone or a silicone network compound in a low-viscosity silicone oil, a volatile silicone oil or another solvent may be added as the silicone resin (K), but in this case, it is desirable to add the solution in such an amount that the amount of the silicone resin (K) is in the above range.

(Other Additives)

To the silicone-modified room temperature-solidifying composition (D) and the cosmetic of the invention, components which are used for usual cosmetics can be added within limits not detrimental to the effects of the present invention. For example, there can be added oil-soluble gelatinizing agents, organic modified clay minerals, resins, antiperspirants, ultraviolet light absorbers, ultraviolet absorbing scattering agents, moisturizing agents, antiseptics, antibacterial agents, perfumes, salts, antioxidants, pH adjusters, chelating agents, refrigerants, anti-inflammatory agents, skin-beautifying components (whitening agent, cell activator, skin roughness improver, blood circulation accelerator, skin astringent, anti-seborrhea agent, etc.), vitamins, amino acids, nucleic acid, hormones, inclusion compounds, and hair styling agents.

Examples of the oil-soluble gelatinizing agents include metallic soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitate, dextrin stearate and dextrin 2-ethylhexanoate palmitate; sucrose fatty acid esters, such as sucrose palmitate and sucrose stearate; fructooligosaccharide fatty acid esters, such as fructooligosaccharide stearate and fructooligosaccharide 2-ethylhexanoate; and benzylidene derivatives of sorbitol, such as monobenzylidene sorbitol and dibenzylidene sorbitol. Examples of the organic modified clay minerals include dimethylbenzyldodecylammonium montmorillonite clay and dimethyldioctadecylammonium montmorillontie clay.

Examples of the antiperspirants include aluminum chlorohydrate, aluminum chloride, aluminum sesquichlorohydrate, zirconyl hydroxychloride, aluminum zirconium hydroxychloride and aluminum zirconium glycine complex.

Examples of the ultraviolet light absorbers include benzoic acid-based ultraviolet light absorbers, such as para-aminobenzoic acid; anthranilic acid-based ultraviolet light absorbers, such as methyl anthranilate; salicylic acid-based ultraviolet light absorbers, such as methyl salicylate; cinnamic acid-based ultraviolet light absorbers, such as octyl paramethoxycinnamate; benzophenone-based ultraviolet light absorbers, such as 2,4-dihydroxybenzophenone; urocanic acid-based ultraviolet light absorbers, such as ethyl urocanate; and dibenzoylmethane-based ultraviolet light absorbers, such as 4-t-butyl-4'-methoxy-dibenzoylmethane.

Examples of the ultraviolet absorbing scattering agents include powders which absorb and scatter ultraviolet light, such as titanium oxide fine particles, iron-containing titanium oxide fine particles, zinc oxide fine particles, cerium oxide fine particles and composites thereof.

Examples of the moisturizing agents include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidonecarboxylate, polyoxyethylene methyl glucoside and polyoxypropylene methyl glucoside.

Examples of the antibacterial antiseptic agents include para-oxybenzoic acid alkyl ester, benzoic acid, sodium benzoate, sorbic acid, potassium sorbate and phenoxyethanol.

Examples of the antibacterial agents include benzoic acid, salicylic acid, carbolic acid, sorbic acid, para-oxybenzoic acid alkyl ester, parachlorometacresol, hexachlorophene, benzalkonium chloride, chlorohexidine chloride, trichlorocarbanilide, photosensitizing dye and phenoxyethanol.

The salts include inorganic salts, organic acid salts, amine salts and amino acid salts. Examples of the inorganic salts include sodium salts, potassium salts, magnesium salts, calcium salts, aluminum salts, zirconium salts and zinc salts of inorganic acids such as hydrochloric acid, sulfuric acid, carboxylic acid and nitric acid. Examples of the organic acid salts include salts of organic acids such as acetic acid, dehydroacetic acid, citric acid, malic acid, succinic acid, ascorbic acid and stearic acid. Examples of the amine salts and the amino acid salts include salts of amines such as triethanolamine, and salts of amino acids such as glutamic acid. Salts of hyaluronic acid, chondroitin sulfuric acid and the like, aluminum zirconium glycine complex, and neutralization salts of acid-alkali which are used in cosmetic formulations are also employable.

Examples of the antioxidants include tocopherol, butylhydroxyanisol, dibutylhydroxytoluene and phytic acid. Examples of the pH adjustors include lactic acid, citric acid, glycolic acid, succinic acid, tartaric acid, dl-malic acid, potassium carbonate, sodium hydrogencarbonate and ammonium hydrogencarbonate. Examples of the chelating agents include alanine, sodium edetate, sodium polyphosphate, sodium metaphosphate and phosphoric acid. Examples of the refrigerants include L-menthol and camphor. Examples of the anti-inflammatory agents include allantoin, glycyrrhizinic acid and salt thereof, glycyrrhetinic acid, stearyl glycyrrhetinate, tranexamic acid, and azulene.

Examples of the skin-beautifying components include whitening agents, such as placental extract, arbutin, glutathione and saxifrage extract; cell activators, such as royal jelly, photosensitizing dye, cholesterol derivative and calf blood extract; skin roughness improvers; blood circulation accelerators, such as nonylic acid vanillylamide, benzyl nicotinate, β-butoxyethyl nicotinate, capsaicine, zingerone, cantharides tincture, ichthammol, caffeine, tannic acid, α-borneol, tocopherol nicotinate, inositol hexaniconate, cyclandelate, cinnarizine, tolazoline, acetylcholine, verapamil, cepharanthine and γ-oryzanol; skin astringents, such as zinc oxide and tannic acid; and anti-seborrhea agent, such as sulfur and thianthol.

Examples of the vitamins include vitamin A, such as vitamin A oil, retinol, retinol acetate and retinol palmitate; vitamin B, specifically, vitamin B2, such as riboflavin, riboflavin butyrate and flavin adenine nucleotide, vitamin B6, such as pyridoxine hydrochloride, pyridoxine dioctanoate and pyridoxine tripalmitate, vitamin B12 and derivatives thereof, and vitamin B15 and derivatives thereof; vitamin C, such as L-ascorbic acid, L-ascorbyl dipalmitate, L-ascorbic acid-2-sodium sulfate and dipotassium L-ascorbic acid phosphate diester; vitamin D, such as ergocalciferol and cholecalciferol; vitamin E, such as α-tocopherol, β-tocopherol, γ-tocopherol, dl-α-tocopherol acetate, dl-α-tocopherol nicotinate and dl-α-tocopherol succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetyl pantothenyl ethyl ether; and biotin.

Examples of the amino acids include glycine, valine, leucine, isoleucine, serine, threonine, phenylalanine, arginine, lysine, aspartic acid, glutamic acid, cystine, cysteine, methionine and tryptophan.

Examples of the nucleic acids include deoxyribonucleic acid.

Examples of the hormones include estradiol and ethenylestradiol.

Examples of the hair-styling high-molecular compounds include amphoteric, anionic, cationic and nonionic high-molecular compounds. Specifically, there can be mentioned polyvinyl pyrrolidone-based high-molecular compounds, such as polyvinyl pyrrolidone and vinyl pyrrolidone/vinyl acetate copolymer; acidic vinyl ether-based high-molecular compounds, such as methyl vinyl ether/maleic anhydride alkyl half-ester copolymer; acidic polyvinyl acetate-based high-molecular compounds, such as vinyl acetate/crotonic acid copolymer; acidic acrylic high-molecular compounds, such as (meth)acrylic acid/alkyl (meth)acrylate copolymer and (meth)acrylic acid/alkyl(meth)acrylate/alkyl acrylamide copolymer; and amphoteric acrylic high-molecular compounds, such as N-methacryloylethyl-N,N-dimethylammonium•α-N-methylcarboxybetaine/alkyl (meth)acrylate copolymer and hydroxypropyl (meth)acrylate/butylaminoethyl methacrylate/acrylic acid octylamide copolymer. Further, natural high-molecular compounds, such as cellulose or derivatives thereof, keratin, and collagen or derivatives thereof, are also preferably employed.

EXAMPLES

The present invention is further described with reference to the following examples, but it should be construed that the invention is in no way limited to those examples. Unless otherwise noted, the term "%" means "% by mass".

Synthesis Example 1

(Synthesis of Olefin Wax)

In a 2-liter stainless steel autoclave thoroughly purged with nitrogen, 1000 ml of hexane and 50 ml of vinyl norbornene (5-vinylbicyclo[2.2.1]hept-2-ene) were placed, and hydrogen was fed until a pressure of 0.3 MPa (gauge pressure). Subsequently, the temperature of the system was raised to 150° C., and then, 0.3 mmol of triisobutylaluminum, 0.004 mmol of triphenylcarbenium tetrakis(pentafluorophenyl)borate and 0.02 mmol of (t-butylamido)dimethyl (tetramethyl-$\eta^5$-cyclopentadienyl)silane titanium dichloride (available from Sigma-Aldrich Co.) were forced into the autoclave with ethylene to initiate polymerization. Thereafter, only ethylene was continuously fed to maintain the total pressure at 2.9 MPa (gauge pressure), and polymerization was performed at 150° C. for 20 minutes. After a small amount of ethanol was added into the system to terminate the polymerization, unreacted ethylene and vinyl norbornene were purged off. The resulting polymer solution was dried overnight at 100° C. under reduced pressure.

Through the above process, an unsaturated group-containing polyethylene wax (A-1) (olefin wax (A-1)) having an unsaturated group number of 11.8 relative to 1,000 carbon atoms, a vinyl norbornene content of 10.1% by weight (unsaturated group content (average)=1.1 groups/molecule), a density of 956 kg/m$^3$, a melting point of 117° C., a penetration hardness of not more than 1, Mn of 1,300, Mw of 3,700 and Mw/Mn of 2.8 was obtained.

Synthesis Example 2

(Synthesis of Olefin Wax)

In a 2-liter stainless steel autoclave thoroughly purged with nitrogen, 950 ml of hexane, 50 ml of propylene and 70 ml of isoprene were placed, and hydrogen was fed until a pressure of 0.2 MPa (gauge pressure). Subsequently, the temperature of the system was raised to 150° C., and then, 0.3 mmol of triisobutylaluminum, 0.004 mmol of triphenylcarbenium tetrakis(pentafluorophenyl)borate and 0.02 mmol of (t-butylamido)dimethyl(tetramethyl-$\eta^5$-cyclopentadienyl)silane titanium dichloride (available from Sigma-Aldrich Co.) were forced into the autoclave with ethylene to initiate polymerization. Thereafter, only ethylene was continuously fed to maintain the total pressure at 2.9 MPa (gauge pressure), and polymerization was performed at 150° C. for 20 minutes. After a small amount of ethanol was added into the system to terminate the polymerization, unreacted ethylene and propylene were purged off. The resulting polymer solution was dried overnight at 100° C. under reduced pressure.

Through the above process, an unsaturated group-containing polyethylene wax (A-2) (olefin wax (A-2)) having an unsaturated group number of 6.0 relative to 1,000 carbon atoms, an isoprene content of 2.4% by weight (unsaturated group content (average)=1.5 groups/molecule), a density of 915 kg/m$^3$, a melting point of 104° C., a penetration hardness of 4, Mn of 3,500, Mw of 5,600 and Mw/Mn of 1.6 was obtained.

Synthesis Example 3

(Synthesis of Olefin Wax)

In a 2-liter stainless steel autoclave thoroughly purged with nitrogen, 950 ml of hexane and 50 ml of vinyl norbornene (5-vinylbicyclo[2.2.1]hept-2-ene) were placed, and hydrogen was fed until a pressure of 0.15 MPa (gauge pressure). Subsequently, the temperature of the system was raised to 150° C., and then, 0.3 mmol of triisobutylaluminum, 0.004 mmol of triphenylcarbenium tetrakis(pentafluorophenyl)borate and 0.02 mmol of (t-butylamido)dimethyl(tetramethyl-$\eta^5$-cyclopentadienyl)silane titanium dichloride (available from Sigma-Aldrich Co.) were forced into the autoclave with ethylene to initiate polymerization. Thereafter, only ethylene was continuously fed to maintain the total pressure at 2.9 MPa (gauge pressure), and polymerization was performed at 150° C. for 20 minutes. After a small amount of ethanol was added into the system to terminate the polymerization, unreacted ethylene and vinyl norbornene were purged off. The resulting polymer solution was dried overnight at 100° C. under reduced pressure.

Through the above process, an unsaturated group-containing polyethylene wax (A-3) (olefin wax (A-3)) having an unsaturated group number of 11.2 relative to 1,000 carbon atoms, a vinyl norbornene content of 9.6% by weight (unsaturated group content (average)=1.2 groups/molecule), a density of 963 kg/m$^3$, a melting point of 125° C., Mn of 1,500, a penetration hardness of not more than 1, Mw of 4,700 and Mw/Mn of 3.1 was obtained.

Synthesis Example 4

(Synthesis of Olefin Wax)

In a 2-liter stainless steel autoclave thoroughly purged with nitrogen, 970 ml of hexane, 30 ml of propylene and 50 ml of vinyl norbornene (5-vinylbicyclo[2.2.1]hept-2-ene) were placed, and hydrogen was fed until a pressure of 0.3 MPa (gauge pressure). Subsequently, the temperature of the system was raised to 150° C., and then, 0.3 mmol of triisobutylaluminum, 0.004 mmol of triphenylcarbenium tetrakis(pentafluorophenyl)borate and 0.02 mmol of (t-butylamido)dimethyl(tetramethyl-$\eta^5$-cyclopentadienyl)silane titanium dichloride (available from Sigma-Aldrich Co.) were forced into the autoclave with ethylene to initiate polymerization. Thereafter, only ethylene was continuously fed to maintain the total pressure at 2.9 MPa (gauge pressure), and polymerization was performed at 150° C. for 20 minutes. After a small amount of ethanol was added into the system to terminate the polymerization, unreacted ethylene and vinyl norbornene were purged off. The resulting polymer solution was dried overnight at 100° C. under reduced pressure.

Through the above process, an unsaturated group-containing polyethylene wax (A-4) (olefin wax (A-4)) having an unsaturated group number of 12.8 relative to 1,000 carbon atoms, a vinyl norbornene content of 11.0% by weight (unsaturated group content (average)=1.1 groups/molecule), a density of 919 kg/m$^3$, a melting point of 107° C., Mn of 1,200, a penetration hardness of 13, Mw of 3,900 and Mw/Mn of 3.3 was obtained.

Synthesis Example 5

(Synthesis of Olefin Wax)

In a 2-liter stainless steel autoclave thoroughly purged with nitrogen, 980 ml of hexane, 20 ml of 1-butene and 20 ml of vinyl norbornene (5-vinylbicyclo[2.2.1]hept-2-ene) were placed, and hydrogen was fed until a pressure of 0.1 MPa (gauge pressure). Subsequently, the temperature of the system was raised to 150° C., and then, 0.3 mmol of triisobutylaluminum, 0.004 mmol of triphenylcarbenium tetrakis(pentafluorophenyl)borate and 0.02 mmol of (t-butylamido)dimethyl(tetramethyl-$\eta^5$-cyclopentadienyl)silane titanium dichloride (available from Sigma Aldrich Co.) were forced into the autoclave with ethylene to initiate polymerization. Thereafter, only ethylene was continuously fed to maintain the total pressure at 2.9 MPa (gauge pressure), and polymerization was performed at 150° C. for 20 minutes. After a small amount of ethanol was added into the system to terminate the polymerization, unreacted ethylene and vinyl norbornene were purged off. The resulting polymer solution was dried overnight at 100° C. under reduced pressure.

Through the above process, an unsaturated group-containing polyethylene wax (A-5) (olefin wax (A-5)) having an unsaturated group number of 5.0 relative to 1,000 carbon atoms, a vinyl norbornene content of 4.3% by weight (unsaturated group content (average)=1.5 groups/molecule), a density of 952 kg/m³, a melting point of 124° C., a penetration hardness of not more than 1, Mn of 4,200, Mw of 11,700 and Mw/Mn of 2.8 was obtained.

Synthesis Example 6

(Synthesis of Olefin Wax)

In a 2-liter stainless steel autoclave thoroughly purged with nitrogen, 900 ml of hexane, 100 ml of 1-butene and 30 ml of vinyl norbornene (5-vinylbicyclo[2.2.1]hept-2-ene) were placed, and hydrogen was fed until a pressure of 0.1 MPa (gauge pressure). Subsequently, the temperature of the system was raised to 150° C., and then, 0.3 mmol of triisobutylaluminum, 0.004 mmol of triphenylcarbenium tetrakis(pentafluorophenyl)borate and 0.02 mmol of (t-butylamido)dimethyl(tetramethyl-η⁵-cyclopentadienyl)silane titanium dichloride (available from Sigma-Aldrich Co.) were forced into the autoclave with ethylene to initiate polymerization. Thereafter, only ethylene was continuously fed to maintain the total pressure at 2.9 MPa (gauge pressure), and polymerization was performed at 150° C. for 20 minutes. After a small amount of ethanol was added into the system to terminate the polymerization, unreacted ethylene and vinyl norbornene were purged off. The resulting polymer solution was dried overnight at 100° C. under reduced pressure.

Through the above process, an unsaturated group-containing polyethylene wax (A-6) (olefin wax (A-6)) having a vinyl norbornene content of 12.0% by weight (unsaturated group content (average)=1.0 group/molecule), a density of 869 kg/m³, a melting point of 68° C., a penetration hardness of not less than 70, Mn of 800, Mw of 2,300 and Mw/Mn of 2.9 was obtained.

Preparation Example 1

130 g of the polyethylene wax (A-1) was mixed together with 310 g of one-terminal hydrogen silicone (1) represented by the following average structural formula, 2 liters of xylene and 0.5 g of a 3% isopropanol solution of chloroplatinic acid, and the reaction was performed under reflux of xylene for 5 hours. The solvent was distilled off by heating under reduced pressure, to give a silicone-modified wax (B-1).

One-terminal hydrogen silicone (1):

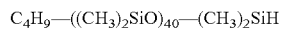

$C_4H_9-((CH_3)_2SiO)_{40}-(CH_3)_2SiH$

Preparation Example 2

A silicone-modified wax (B-2) was obtained in the same manner as in Preparation Example 1, except that the one-terminal hydrogen silicone (1) was changed to 240 g of one-terminal hydrogen silicone (2) represented by the following average structural formula.

One-terminal hydrogen silicone (2):

$C_4H_9-((CH_3)_2SiO)_{30}-(CH_3)_2SiH$

Preparation Example 3

A silicone-modified wax (B-3) was obtained in the same manner as in Preparation Example 1, except that the one-terminal hydrogen silicone (1) was changed to 80 g of hydrogen silicone (3) represented by the following average structural formula.

Hydrogen silicone (3):

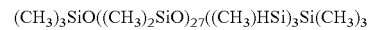

$(CH_3)_3SiO((CH_3)_2SiO)_{27}((CH_3)HSi)_3Si(CH_3)_3$

Preparation Example 4

A silicone-modified wax (B-4) was obtained in the same manner as in Preparation Example 1, except that the one-terminal hydrogen silicone (1) was changed to 25 g of hydrogen silicone (4) represented by the following average structural formula.

Hydrogen silicone (3):

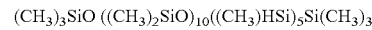

$(CH_3)_3SiO((CH_3)_2SiO)_{10}((CH_3)HSi)_5Si(CH_3)_3$

Preparation Example 5

A silicone-modified wax (B-5) was obtained in the same manner as in Preparation Example 1, except that the polyethylene wax (A-1) was changed to 350 g of the polyethylene wax (A-2).

Preparation Example 6

A silicone-modified wax (B-6) was obtained in the same manner as in Preparation Example 1, except that the polyethylene wax (A-1) was changed to 150 g of the polyethylene wax (A-3).

Preparation Example 7

A silicone-modified wax (B-7) was obtained in the same manner as in Preparation Example 1, except that the polyethylene wax (A-1) was changed to 120 g of the polyethylene wax (A-4).

Preparation Example 8

A silicone-modified wax (B-8) was obtained in the same manner as in Preparation Example 1, except that the polyethylene wax (A-1) was changed to 420 g of the polyethylene wax (A-5).

Comparative Preparation Example 1

A silicone-modified wax (B-9) was obtained in the same manner as in Preparation Example 3, except that the polyethylene wax (A-1) was changed to 80 g of the polyethylene wax (A-6).

Example 1

50 Parts by mass of the silicone-modified wax (B-1) and 50 parts by mass of dimethylpolysiloxane (10 mm²/sec, 25° C.) were heated to be molten and then homogeneously stirred to prepare a silicone-modified room temperature-solidifying composition. Then, the resulting composition was evaluated on solidification properties at room temperature.

Solidification Properties at Room Temperature:

When a silicone-modified room temperature-solidifying composition was cooled to room temperature, the composition which was solid and had no fluidity was evaluated as "A", and the composition which had fluidity was evaluated as "B".

Examples 2 to 10

Silicone-modified room temperature-solidifying compositions were prepared in the same manner as in Example 1, except that blending of the components was changed as shown in Table 1. Then, the resulting compositions were evaluated on solidification properties at room temperature. The results are set forth in Table 1. The unit of each numerical value in the table is "part(s) by mass".

Comparative Examples 1 to 4

Silicone-modified room temperature-solidifying compositions were prepared in the same manner as in Example 1, except that blending of the components was changed as shown in Table 2. Then, the resulting compositions were evaluated on solidification properties at room temperature. The results are set forth in Table 2. The unit of each numerical value in the table is "part(s) by mass".

TABLE 1

|  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Silicone-modified wax (B-1) | 50 | 60 | 40 |  |  |  | 25 |  |  |  |
| Silicone-modified wax (B-2) |  |  |  | 70 |  |  |  |  |  |  |
| Silicone-modified wax (B-3) |  |  |  |  | 50 |  |  |  |  |  |
| Silicone-modified wax (B-4) |  |  |  |  |  | 60 |  |  |  |  |
| Silicone-modified wax (B-5) |  |  |  |  |  |  | 25 |  |  |  |
| Silicone-modified wax (B-6) |  |  |  |  |  |  |  | 40 |  |  |
| Silicone-modified wax (B-7) |  |  |  |  |  |  |  |  | 80 |  |
| Silicone-modified wax (B-8) |  |  |  |  |  |  |  |  |  | 20 |
| Silicone-modified wax (B-9) |  |  |  |  |  |  |  |  |  |  |
| Dimethylpolysiloxane (10 mm²/s, 25° C.) | 50 | 40 | 60 | 30 | 50 | 40 | 50 | 60 | 20 | 80 |
| Solidification properties at room temperature | A | A | A | A | A | A | A | A | A | A |

TABLE 2

|  | Comp. Ex. 1 | Comp. Ex. 2 | Comp. Ex. 3 | Comp. Ex. 4 |
|---|---|---|---|---|
| Silicone-modified wax (B-1) | 3 | 97 |  |  |
| Silicone-modified wax (B-2) |  |  |  |  |
| Silicone-modified wax (B-3) |  |  |  |  |
| Silicone-modified wax (B-4) |  |  |  |  |
| Silicone-modified wax (B-5) |  |  |  |  |
| Silicone-modified wax (B-6) |  |  |  |  |
| Silicone-modified wax (B-7) |  |  |  |  |
| Silicone-modified wax (B-8) |  |  |  |  |
| Silicone-modified wax (B-9) |  |  | 50 | 70 |
| Dimethylpolysiloxane (10 mm²/s, 25° C.) | 97 | 3 | 50 | 30 |
| Solidification properties at room temperature | B | B | B | B |

Preparation Example 9

A silicone-modified wax (B-10) was obtained in the same manner as in Preparation Example 2, except that the amount of the one-terminal hydrogen silicone (2) was changed to 105 g from 240 g.

Preparation Example 10

A silicone-modified wax (B-11) was obtained in the same manner as in Preparation Example 6, except that the one-terminal hydrogen silicone (1) was changed to 150 g of the one-terminal hydrogen silicone (2).

Preparation Example 11

A silicone-modified wax (B-12) was obtained in the same manner as in Preparation Example 10, except that the polyethylene wax (A-3) was changed to 150 g of the polyethylene wax (A-4).

Example 11

| (Emulsion) | |
|---|---|
| (Components) | Mass (%) |
| 1. Silicone-modified wax (B-10) | 2.0 |
| 2. Dimethylpolysiloxane (6 mm²/sec (25° C.)) | 30.0 |
| 3. Decamethylcyclopentasiloxane | 10.0 |

-continued

| (Emulsion) | |
|---|---|
| (Components) | Mass (%) |
| 4. Glyceryl trioctanoate | 5.0 |
| 5. Polyether-modified silicone*[1] | 5.0 |
| 6. 1,3-Butylene glycol | 5.0 |
| 7. Antiseptic | proper amount |
| 8. Perfume | proper amount |
| 9. Purified water | 43.0 |

*[1] KF-6017 (trade name), available from Shin-Etsu Chemical Co., Ltd.

(Preparation Process)

(A) The components 1 to 5 were heated to dissolve.

(B) The components 6 to 7 and 9 were mixed, then the mixture was added to the dissolution product obtained in the step (A), and they were emulsified.

(C) The emulsion obtained in the step (B) was cooled, and the component 8 was added to give an emulsion.

It was confirmed that the emulsion obtained as above was free from tackiness, spread lightly, gave a good feeling of close adhesion, had good stability and gave glossy finish.

Example 12

(Water-in-Oil Cream)

| (Components) | Mass (%) |
|---|---|
| 1. Dimethylpolysiloxane (6 mm$^2$/sec (25° C.)) | 10.0 |
| 2. Decamethylcyclopentasiloxane | 7.0 |
| 3. Glyceryl trioctanoate | 5.0 |
| 4. Polyether-modified branched silicone*[1] | 2.0 |
| 5. Silicone-modified wax (B-12) | 1.0 |
| 6. Dipropylene glycol | 7.0 |
| 7. Antiseptic | proper amount |
| 8. Perfume | proper amount |
| 9. Purified water | 68.0 |

*[1]KF-6028 (trade name), available from Shin-Etsu Chemical Co., Ltd.

(Preparation Process)

(A) The components 1 to 5 were mixed with heating.

(B) The components 6 to 9 were mixed, then the mixture was added to the mixture obtained in the step (A), and they were stirred to emulsify.

It was confirmed that the water-in-oil cream obtained as above was free from oiliness and tackiness, spread lightly, was refreshing, gave a good feeling of close adhesion, had good stability and gave glossy finish.

Example 13

(Water-in-Oil Cream)

| (Components) | Mass (%) |
|---|---|
| 1. Silicone-modified wax (B-10) | 2.0 |
| 2. Dimethylpolysiloxane (6 mm$^2$/sec (25° C.)) | 10.0 |
| 3. Crosslinkable polyether-modified silicone*[1] | 5.0 |
| 4. Dipropylene glycol | 10.0 |
| 5. Sodium citrate | 0.2 |
| 6. Ethanol | 5.0 |
| 7. Antiseptic | proper amount |
| 8. Perfume | proper amount |
| 9. Purified water | 67.8 |

*[1]KSG-21 (trade name), available from Shin-Etsu Chemical Co., Ltd.

(Preparation Process)

(A) The components 1 to 3 were heated to dissolve.

(B) The components 4 to 9 were mixed to dissolve, then the dissolution product was added to the dissolution product obtained in the step (A), and they were stirred to emulsify.

It was confirmed that the water-in-oil cream obtained as above was free from oiliness and tackiness, spread lightly, was fresh and refreshing in use, gave a good feeling of close adhesion, had good stability and gave matte finish.

Example 14

(Water-in-Oil Make-Up Foundation)

| (Components) | Mass (%) |
|---|---|
| 1. Crosslinkable polyether-modified silicone*[1] | 4.0 |
| 2. Crosslinkable dimethylpolysiloxane*[2] | 1.0 |
| 3. Polyether-modified silicone*[3] | 0.5 |
| 4. Dimethylpolysiloxane (6 mm$^2$/sec (25° C.)) | 6.0 |
| 5. Dimethylpolysiloxane (20 mm$^2$/sec (25° C.)) | 2.0 |
| 6. Decamethylcyclopentasiloxane | 3.0 |
| 7. Titanium oxide/cyclopentasiloxane dispersion*[4] | 10.0 |
| 8. Silicone-modified wax (B-12) | 1.0 |
| 9. Dipropylene glycol | 5.0 |
| 10. Sodium citrate | 0.2 |
| 11. Methyl cellulose (2% aqueous solution)*[5] | 2.5 |
| 12. Ethanol | 3.0 |
| 13. Antiseptic | proper amount |
| 14. Perfume | proper amount |
| 15. Purified water | 61.8 |

*[1]KSG-21 (trade name), available from Shin-Etsu Chemical Co., Ltd.
*[2]KSG-15 (trade name), available from Shin-Etsu Chemical Co., Ltd.
*[3]KF-6017 (trade name), available from Shin-Etsu Chemical Co., Ltd.
*[4]SPD-T1S (trade name), available from Shin-Etsu Chemical Co., Ltd.
*[5]Metolose 65-SH4000 (trade name), available from Shin-Etsu Chemical Co., Ltd.

(Preparation Process)

(A) The components 1 to 8 were mixed with heating.

(B) The components 9 to 15 were mixed to dissolve, then the dissolution product was added to the mixture obtained in the step (A), and they were stirred to emulsify.

It was confirmed that the water-in-oil make-up foundation obtained as above was free from oiliness and tackiness, spread lightly, was fresh and refreshing in use, gave a good feeling of close adhesion, had good stability, gave matte finish, and had ultraviolet light protection effect and excellent make-up lasting properties.

Example 15

(Oil-in-Water Cream)

| (Components) | Mass (%) |
|---|---|
| 1. Silicone-modified wax (B-11) | 2.0 |
| 2. Crosslinkable dimethylpolysiloxane*[1] | 15.0 |
| 3. Decamethylcyclopentasiloxane | 10.0 |
| 4. Dimethylpolysiloxane (6 mm$^2$/sec (25° C.)) | 18.0 |
| 5. Polyether-modified silicone*[2] | 0.7 |
| 6. Propylene glycol | 3.0 |
| 7. Polyacrylamide-based mixture*[3] | 0.8 |
| 8. Xanthan gum (2% aqueous solution) | 8.0 |
| 9. Antiseptic | proper amount |
| 10. Perfume | proper amount |
| 11. Purified water | 42.5 |

*[1]KSG-16 (trade name), available from Shin-Etsu Chemical Co., Ltd.
*[2]KF-6011 (trade name), available from Shin-Etsu Chemical Co., Ltd.
*[3]Sepigel 305 (trade name), available from SEPIC Co.

(Preparation Process)

(A) The components 1 to 4 were mixed with heating.

(B) The components 5 to 11 were mixed to dissolve.

(C) The mixture obtained in the step (A) was added to the dissolution product obtained in the step (B), and they were stirred to emulsify.

It was confirmed that the oil-in-water cream obtained as above was excellent in light spread and refreshing in use.

Example 16

(Water-in-Oil Solid Cream)

| (Components) | Mass (%) |
| --- | --- |
| 1. Silicone-modified wax (B-10) | 30.0 |
| 2. Dimethylpolysiloxane (6 mm$^2$/sec (25° C.)) | 24.0 |
| 3. Decamethylcyclopentasiloxane | 24.0 |
| 4. Polyether-modified silicone*[1] | 2.0 |
| 5. 1,3-Butylene glycol | 2.0 |
| 6. Antiseptic | proper amount |
| 7. Perfume | proper amount |
| 8. Purified water | 18.0 |

*[1]KF-6017 (trade name), available from Shin-Etsu Chemical Co., Ltd.

(Preparation Process)

(A) The components 1 to 4 were heated to dissolve.

(B) The components 5 to 8 were mixed to dissolve, then the dissolution product was added to the dissolution product obtained in the step (A), and they were stirred to emulsify.

(C) The emulsion obtained in the step (B) was filled to give a cosmetic product.

It was confirmed that the water-in-oil solid cream obtained as above was free from oiliness and tackiness though the amount of the oil agent was large, and was excellent in light spread and refreshing in use, gave a good feeling of close adhesion and had good stability.

Example 17

(Lipstick)

| (Components) | Mass (%) |
| --- | --- |
| 1. Silicone-modified wax (B-12) | 40.0 |
| 2. Dimethylpolysiloxane (6 mm$^2$/sec (25° C.)) | 30.0 |
| 3. Decamethylcyclopentasiloxane | 26.0 |
| 4. Acrylic silicone resin*[1] | 4.0 |
| 5. Pigment | proper amount |
| 6. Antiseptic | proper amount |
| 7. Perfume | proper amount |

*[1]KP-545 (trade name), available from Shin-Etsu Chemical Co., Ltd.

(Preparation Process)

(A) The components 1 to 3 were heated to dissolve.

(B) The components 4 to 6 were mixed to disperse, then the dispersion was added to the dissolution product obtained in the step (A), and they were homogeneously stirred.

(C) The component 7 was added to the dissolution product obtained in the step (B), and the mixture was filled to give a cosmetic product.

It was confirmed that the lipstick obtained as above was free from oiliness and tackiness, slid lightly, spread well, gave a good feeling of close adhesion, had good stability and had excellent make-up lasting properties.

Example 18

(Powder Foundation)

| (Components) | Mass (%) |
| --- | --- |
| 1. Sericite | 40.0 |
| 2. Mica | 10.0 |
| 3. Talc | balance |
| 4. Titanium oxide | 10.0 |
| 5. Titanium oxide fine particle | 5.0 |
| 6. Magnesium stearate | 3.0 |
| 7. Pigment | 4.2 |
| 8. Silicone-modified wax (B-10) | 1.0 |
| 9. Dimethylpolysiloxane (6 mm$^2$/sec (25° C.)) | 3.0 |
| 10. Antiseptic | proper amount |
| 11. Perfume | proper amount |

(Preparation Process)

(A) The components 8 to 11 were mixed.

(B) The components 1 to 7 were mixed, then to the mixture, the mixture obtained in the step (A) was added, and they were homogeneously stirred.

(C) The mixture obtained in the step (B) was press molded in a mold to give a powder foundation.

It was confirmed that the powder foundation obtained as above was free from tackiness, spread lightly, gave a good feeling of close adhesion, had good stability and gave glossy finish.

Example 19

(Cream Foundation)

| (Components) | Mass (%) |
| --- | --- |
| 1. Crosslinkable polyether-modified silicone*[1] | 4.0 |
| 2. Glyceryl trioctanoate | 3.0 |
| 3. Dimethylpolysiloxane (6 mm$^2$/sec (25° C.)) | 5.0 |
| 4. Decamethylcyclopentasiloxane | 6.0 |
| 5. Silicone-modified wax (B-11) | 2.0 |
| 6. Fluorine-modified hybrid silicone composite powder*[2] | 2.5 |
| 7. Pigment | 8.0 |
| 8. Acrylic silicone resin*[3] | 5.0 |
| 9. Dipropylene glycol | 5.0 |
| 10. Sodium citrate | 0.2 |
| 11. Antiseptic | proper amount |
| 12. Perfume | proper amount |
| 13. Purified water | 59.3 |

*[1]KSG-21 (trade name), available from Shin-Etsu Chemical Industry Co., Ltd.
*[2]KSP-200 (trade name), available from Shin-Etsu Chemical Industry Co., Ltd.
*[3]KP-545 (trade name), available from Shin-Etsu Chemical Industry Co., Ltd.

(Preparation Process)

(A) The components 1 to 6 were mixed with heating.

(B) The components 9 to 13 were mixed to dissolve, then the dissolution product was added to the mixture obtained in the step (A), and they were stirred to emulsify.

(C) The components 7 and 8 were mixed, then the mixture was added to the emulsion obtained in the step (B), and homogenized.

It was confirmed that the cream foundation obtained as above was free from tackiness, spread lightly, gave a good feeling of close adhesion, had good stability and gave matte finish.

Example 20

(Solid Foundation)

| (Components) | Mass (%) |
|---|---|
| 1. Silicone-modified wax (B-12) | 30.0 |
| 2. Polyethylene wax | 5.0 |
| 3. Dimethylpolysiloxane (6 mm$^2$/sec (25° C.)) | 32.5 |
| 4. Decamethylcyclopentasiloxane | 28.5 |
| 5. Acrylic silicone resin*[1] | 4.0 |
| 6. Pigment | proper amount |
| 7. Antiseptic | proper amount |
| 8. Perfume | proper amount |

*[1]KP-545 (trade name), available from Shin-Etsu Chemical Co., Ltd.

(Preparation Process)

(A) The components 1 to 4 were heated to dissolve.

(B) The components 5 to 7 were mixed to disperse, then the dispersion was added to the dissolution product obtained in the step (A), and they were homogeneously stirred.

(C) The component 8 was added to the dissolution product obtained in the step (B), and the mixture was filled to give a cosmetic product.

It was confirmed that the solid foundation obtained as above was free from oiliness and tackiness, slid lightly, spread well, gave a good feeling of close adhesion, had good stability and had excellent make-up lasting properties.

Example 21

(Water-in-Oil Compact Foundation)

| (Components) | Mass (%) |
|---|---|
| 1. Silicone-modified wax (B-10) | 30.0 |
| 2. Dimethylpolysiloxane (6 mm$^2$/sec (25° C.)) | 24.0 |
| 3. Decamethylcyclopentasiloxane | 22.0 |
| 4. Acrylic silicon resin*[1] | 4.0 |
| 5. Trimethylsiloxysilicate*[2] | 1.0 |
| 6. Polyether-modified silicone*[3] | 2.0 |
| 7. Pigment | proper amount |
| 8. 1,3-Butylene glycol | 2.0 |
| 9. Antiseptic | proper amount |
| 10. Perfume | proper amount |
| 11. Purified water | 15.0 |

*[1]KP-545 (trade name), available from Shin-Etsu Chemical Co., Ltd.
*[2]KF-7312J (trade name), available from Shin-Etsu Chemical Co., Ltd.
*[3]KF-6017 (trade name), available from Shin-Etsu Chemical Co., Ltd.

(Preparation Process)

(A) The components 1 to 5 were heated to dissolve.

(B) The components 8, 9 and 11 were mixed to dissolve, then the dissolution product was added to the dissolution product obtained in the step (A), and they were stirred to emulsify.

(C) The components 6 and 7 were mixed and thereby dispersed, then the dispersion was added to the emulsion obtained in the step (B), and they were homogeneously stirred.

(D) The component 10 was added to the emulsion obtained in the step (C), and the mixture was filled to give a cosmetic product.

It was confirmed that the water-in-oil compact foundation obtained as above was free from oiliness and tackiness though the amount of the oil agent was large, spread lightly, was refreshing in use, gave a good feeling of close adhesion, had good stability and had excellent make-up lasting properties.

Example 22

(Eye Shadow)

| (Components) | Mass (%) |
|---|---|
| 1. Sericite | 40.0 |
| 2. Mica | 10.0 |
| 3. Talc | balance |
| 4. Titanium oxide | 10.0 |
| 5. Titanium oxide fine particle | 5.0 |
| 6. Magnesium stearate | 3.0 |
| 7. Pigment | proper amount |
| 8. Octyldodecanol | 3.0 |
| 9. Dimethylpolysiloxane (6 mm$^2$/sec (25° C.)) | 8.0 |
| 10. Silicone-modified wax (B-11) | 2.0 |
| 11. Antiseptic | proper amount |
| 12. Perfume | proper amount |

(Preparation Process)

(A) The components 8 to 11 were mixed with heating.

(B) The components 1 to 7 were mixed, then to the mixture, the mixture obtained in the step (A) was added, and they were homogeneously stirred.

(C) The component 14 was added to the mixture obtained in the step (B).

It was confirmed that the eye shadow obtained as above was free from tackiness, spread lightly, gave a good feeling of close adhesion, had good stability, gave glossy finish and had excellent make-up lasting properties.

Example 23

(Eyebrow Powder)

| (Components) | Mass (%) |
|---|---|
| 1. Silicone-modified wax (B-12) | 3.0 |
| 2. Dimethylpolysiloxane (6 mm$^2$/sec (25° C.)) | 5.0 |
| 3. Glyceryl triactanoate | 2.0 |
| 4. Silicone treated mica | 40.0 |
| 5. Silicone treated barium sulfate | 15.0 |
| 6. Silicone treated titanium oxide | 10.0 |
| 7. Silicone treated pigment | proper amount |
| 8. Hybrid silicone composite powder*[1] | 1.5 |
| 9. Spherical polymethylsilsesquioxane powder*[2] | 2.5 |
| 10. Silicone treated talc | balance |
| 11. Antiseptic | proper amount |
| 12. Perfume | proper amount |

*[1]KSP-100 (trade name), available from Shin-Etsu Chemical Co., Ltd.
*[2]KMP-590 (trade name), available from Shin-Etsu Chemical Co., Ltd.

(Preparation Process)

(A) The components 4 to 12 were mixed and homogenized.

(B) The components 1 to 3 were mixed to dissolve, then the dissolution product was added to the mixture obtained in the step (A), and they were homogenized.

(C) The mixture obtained in the step (B) was press molded in a mold to give an eyebrow powder.

It was confirmed that the eyebrow powder obtained as above was free from tackiness, spread lightly, gave a good feeling of close adhesion, had good stability, gave glossy finish and had excellent make-up lasting properties.

Example 24

(Eyebrow Pencil)

| (Components) | Mass (%) |
| --- | --- |
| 1. Silicone-modified wax (B-10) | 40.0 |
| 2. Polyethylene wax | 10.0 |
| 3. Dimethylpolysiloxane (6 mm$^2$/sec (25° C.)) | 40.0 |
| 4. Decamethylcyclopentasiloxane | 5.0 |
| 5. Acrylic silicone resin*[1] | 5.0 |
| 6. Pigment | proper amount |
| 7. Antiseptic | proper amount |
| 8. Perfume | proper amount |

*[1]KP-545 (trade name), available from Shin-Etsu Chemical Co., Ltd.

(Preparation Process)

(A) The components 1 to 4 were heated to dissolve.

(B) The components 5 to 7 were mixed to disperse, then the dispersion was added to the dissolution product obtained in the step (A), and they were homogeneously stirred.

(C) The component 8 was added to the dissolution product obtained in the step (B), and the mixture was filled to give a cosmetic product.

It was confirmed that the eyebrow pencil obtained as above was free from powder-scattering, had excellent sliding properties and had excellent make-up lasting properties.

Example 25

(Hair Cream)

| (Components) | Mass (%) |
| --- | --- |
| 1. Silicone-modified room temperature-solidifying composition obtained in Example 1 | 4.0 |
| 2. Dimethylpolysiloxane (6 mm$^2$/sec (25° C.)) | 1.0 |
| 3. Decamethylcyclopentasiloxane | 8.0 |
| 4. Stearyl trimethyl ammonium chloride | 1.5 |
| 5. Glycerin | 3.0 |
| 6. Propylene glycol | 5.0 |
| 7. Hydroxyethyl cellulose | 0.2 |
| 8. Antiseptic | proper amount |
| 9. Perfume | proper amount |
| 10. Purified water | 75.3 |

(Preparation Process)

(A) The components 1 to 3 were heated to dissolve.

(B) The components 4 to 8 and 10 were homogeneously mixed to dissolve.

(C) The dissolution product obtained in the step (B) was added to the dissolution product obtained in the step (A), the mixture was emulsified and then cooled, and the component 9 was added.

It was confirmed that the hair cream obtained as above exerted very excellent effects in the spreadability when applied and in the softness, smoothness, stability, moist touch and shine after used, so that this hair cream was synthetically very excellent.

Example 26

(Conditioning Mousse)

| (Components) | Mass (%) |
| --- | --- |
| 1. Silicone-modified wax (B-12) | 0.5 |
| 2. Dimethylpolysiloxane (6 mm$^2$/sec (25° C.)) | 2.0 |
| 3. Crosslinkable dimethylpolysiloxane*[1] | 0.5 |
| 4. Glycerol trioctanoate | 1.5 |
| 5. Glycerin | 3.0 |
| 6. Stearyl dimethylbenzyl ammonium chloride | 0.5 |
| 7. Polyoxyethylene hydrogenated castor oil | 0.5 |
| 8. Ethanol | 7.0 |
| 9. Antiseptic | proper amount |
| 10. Perfume | proper amount |
| 11. Purified water | balance |
| 12. Liquefied petroleum gas | 5.0 |

*[1]KSG-16 (trade name), available from Shin-Etsu Chemical Co., Ltd.

(Preparation Process)

(A) The components 1 to 4 were heated to dissolve.

(B) The components 5 to 9 and 11 were homogeneously mixed to dissolve.

(C) The dissolution product obtained in the step (B) was added to the dissolution product obtained in the step (A), the mixture was emulsified and then cooled, and the component 10 was added.

(D) The emulsion obtained in the step (C) was filled in an aerosol can to give a conditioning mousse.

It was confirmed that the conditioning mousse obtained as above was excellent in the moist touch, softness and smoothness, was favorable to the touch without oiliness, gave a good feeling of close adhesion, had good stability and gave matte finish.

Example 27

(Roll-on Antiperspirant)

| (Components) | Mass (%) |
| --- | --- |
| 1. Silicone-modified wax (B-11) | 5.0 |
| 2. Crosslinkable polyether-modified silicone*[1] | 20.0 |
| 3. Dimethylpolysiloxane (6 mm$^2$/sec (25° C.)) | 10.0 |
| 4. Crosslinkable dimethylpolysiloxane*[2] | 15.0 |
| 5. Decamethylcyclopentasiloxane | 30.0 |
| 6. Aluminum zirconium tetrachlorohydrate | 20.0 |
| 7. Perfume | proper amount |

*[1]KSG-21 (trade name), available from Shin-Etsu Chemical Co., Ltd.
*[2]KSG-15 (trade name), available from Shin-Etsu Chemical Co., Ltd.

(Preparation Process)

(A) The components 1 to 5 were mixed with heating.

(B) The components 6 and 7 were added to the mixture obtained in the step (A), and they were homogeneously dispersed.

It was confirmed that the roll-on antiperspirant obtained as above spread lightly, gave a feeling of refreshment, was free from tackiness and oiliness, had no change with temperature or time, and had very excellent usability and stability.

Example 28

(Water-in-Oil Antiperspirant)

| (Components) | Mass (%) |
|---|---|
| 1. Silicone-modified wax (B-11) | 2.0 |
| 2. Crosslinkable polyether-modified silicone*[1] | 7.0 |
| 3. Decamethylcyclopentasiloxane | 7.0 |
| 4. Glyceryl trioctanoate | 8.0 |
| 5. 1,3-Butylene glycol | 5.0 |
| 6. Sodium citrate | 0.2 |
| 7. Aluminum chlorohydrate | 20.0 |
| 8. Perfume | proper amount |
| 9. Purified water | 50.8 |

*[1]KSG-21 (trade name), available from Shin-Etsu Chemical Co., Ltd.

(Preparation Process)

(A) The components 1 to 4 were mixed with heating.

(B) The components 5, 6 and 8 were mixed, to the mixture, the components 7 and 8 were added, and they were dissolved.

(C) The dissolution product obtained in the step (B) was added to the mixture obtained in the step (A), and they were stirred to emulsify.

It was confirmed that the water-in-oil antiperspirant obtained as above spread lightly, gave a feeling of refreshment, was free from tackiness and oiliness, had no change with temperature or time, and had very excellent usability and stability.

Example 29

(Solid Antiperspirant)

| (Components) | Mass (%) |
|---|---|
| 1. Silicone-modified wax (B-10) | 22.0 |
| 2. Polyethylene wax | 4.0 |
| 3. Dimethylpolysiloxane (6 mm$^2$/sec (25° C.)) | 22.0 |
| 4. Decamethylcyclopentasiloxane | 22.0 |
| 5. Crosslinkable dimethylpolysiloxane*[1] | 15.0 |
| 6. Aluminum zirconium tetrachlorohydrate | 15.0 |
| 7. Perfume | proper amount |

*[1]KSG-16 (trade name), available from Shin-Etsu Chemical Co., Ltd.

(Preparation Process)

(A) The components 1 to 5 were homogenized with heating.

(B) The components 6 and 7 were mixed with the mixture obtained in the step (A) to disperse.

(C) The mixture obtained in the step (B) was filled to give a cosmetic product.

It was confirmed that the solid antiperspirant obtained as above spread lightly, gave a feeling of refreshment, was free from tackiness and oiliness, had no change with temperature or time, and had very excellent usability and stability.

Example 30

(Solid Antiperspirant)

| (Components) | Mass (%) |
|---|---|
| 1. Silicone-modified wax (B-10) | 26.0 |
| 2. Dimethylpolysiloxane (6 mm$^2$/sec (25° C.)) | 22.0 |
| 3. Decamethylcyclopentasiloxane | 22.0 |
| 4. Crosslinkable dimethylpolysiloxane*[1] | 15.0 |
| 5. Aluminum zirconium tetrachlorohydrate (glycine salt) | 15.0 |
| 6. Perfume | proper amount |

*[1]KSG-16 (trade name), available from Shin-Etsu Chemical Co., Ltd.

(Preparation Process)

(A) The components 1 to 4 were homogenized with heating.

(B) The components 5 and 6 were mixed with the mixture obtained in the step (A) to disperse.

(C) The mixture obtained in the step (B) was filled to give a cosmetic product.

It was confirmed that the solid antiperspirant obtained as above spread lightly, gave a feeling of refreshment, was free from tackiness and oiliness, had no change with temperature or time, and had very excellent usability and stability.

Example 31

(UV-Protection Water-in-Oil Cream)

| (Components) | Mass (%) |
|---|---|
| 1. Silicone treated zinc oxide | 20.0 |
| 2. Acrylate/dimethyl silicone copolymer*[1] | 12.0 |
| 3. Decamethylcyclopentasiloxane | 20.0 |
| 4. Glyceryl trioctanoate | 3.0 |
| 5. Silicone modified wax (B-12) | 2.0 |
| 6. Crosslinkable polyether-modified silicone*[2] | 5.0 |
| 7. Polyether-modified silicone*[3] | 1.0 |
| 8. Alkyl/polyether comodified silicone*[4] | 1.0 |
| 9. Octyl methoxycinnamate | 6.0 |
| 10. Sodium citrate | 0.2 |
| 11. Dipropylene glycol | 3.0 |
| 12. Antiseptic | proper amount |
| 13. Perfume | proper amount |
| 14. Purified water | 26.8 |

*[1]KP-545 (trade name), available from Shin-Etsu Chemical Co., Ltd.
*[2]KSG-21 (trade name), available from Shin-Etsu Chemical Co., Ltd.
*[3]KF-6017 (trade name), available from Shin-Etsu Chemical Co., Ltd.
*[4]KF-6026 (trade name), available from Shin-Etsu Chemical Co., Ltd.

(Preparation Process)

(A) A part of the component 3 and the components 4 to 9 were mixed with heating.

(B) The components 10 to 12 and 14 were mixed, then the mixture was added to the mixture obtained in the step (A), and they were stirred to emulsify.

(C) The components 1 and 2 and the remainder of the component 3 were mixed with the emulsion obtained in the step (B) to disperse, then the component 13 was further added, and the mixture was homogenized.

It was confirmed that the water-in-oil UV-protection cream obtained as above spread lightly, was refreshing, was free from tackiness and oiliness, had transparency and excellent make-up lasting properties, had no change with temperature or time, and had very excellent usability and stability.

Example 32

(UV-Protection Water-in-Oil Emulsion)

| (Components) | Mass (%) |
| --- | --- |
| 1. Dimethylpolysiloxane (6 mm$^2$/sec (25° C.)) | 5.0 |
| 2. Crosslinkable polyether-modified silicone*[1] | 5.0 |
| 3. Glyceryl trioctanoate | 2.0 |
| 4. Silicone-modified wax (B-12) | 1.0 |
| 5. Polyether-modified silicone*[2] | 1.0 |
| 6. Titanium oxide/decamethylcyclopentasiloxane dispersion*[3] | 30.0 |
| 7. Zinc oxide/decamethylcyclopentasiloxane dispersion*[4] | 30.0 |
| 8. Dipropylene glycol | 3.0 |
| 9. Sodium citrate | 0.2 |
| 10. Antiseptic | proper amount |
| 11. Perfume | proper amount |
| 12. Purified water | 22.8 |

*[1]KSG-21 (trade name), available from Shinetsu Chemical Industry Co., Ltd.
*[2]KF-6017 (trade name), available from Shinetsu Chemical Industry Co., Ltd.
*[3]SPD-TIS (trade name), available from Shinetsu Chemical Industry Co., Ltd.
*[4]SPD-ZI (trade name), available from Shinetsu Chemical Industry Co., Ltd.

(Preparation Process)

(A) The components 1 to 5 were mixed with heating.

(B) The components 8 to 10 and 12 were mixed to dissolve, then the dissolution product was added to the mixture obtained in the step (A), and they were stirred to emulsify.

(C) The components 6, 7 and 11 were added to the emulsion obtained in the step (B), and they were homogenized.

It was confirmed that the water-in-oil UV-protection emulsion obtained as above spread lightly, was refreshing, was free from tackiness and oiliness, had transparency and excellent make-up lasting properties, had no change with temperature or time, and had very excellent usability and stability.

Example 33

(UV-Protection Oil-in-Water Cream)

| (Components) | Mass (%) |
| --- | --- |
| 1. Crosslinkable organopolysiloxane*[1] | 5.0 |
| 2. Cetyl isooctanoate | 5.0 |
| 3. Silicone-modified wax (B-11) | 1.0 |
| 4. Titanium oxide/decamethylcyclopentasiloxane dispersion*[2] | 15.0 |
| 5. Polyether-modified silicone*[3] | 1.0 |
| 6. Polyether-modified silicone*[4] | 1.0 |
| 7. Acrylamide-based mixture*[5] | 2.0 |
| 8. Propylene glycol | 5.0 |
| 9. Methyl cellulose (2% aqueous solution)*[6] | 5.0 |
| 10. Antiseptic | proper amount |
| 11. Perfume | proper amount |
| 12. Purified water | 60.0 |

*[1]KSG-18 (trade name), available from Shin-Etsu Chemical Co., Ltd.
*[2]SPD-T1S (trade name), available from Shin-Etsu Chemical Co., Ltd.
*[3]KF-6027 (trade name), available from Shin-Etsu Chemical Co., Ltd.
*[4]KF-6011 (trade name), available from Shin-Etsu Chemical Co., Ltd.
*[5]Sepigel 305 (trade name), available from SEPIC Co.
*[6]Metolose SM-4000 (trade name), available from Shin-Etsu Chemical Co., Ltd.

(Preparation Process)

(A) The components 5 to 8, 10 and 12 were mixed.

(B) The components 1 to 3 were mixed with heating, then the mixture was added to the mixture obtained in the step (A), and they were stirred to emulsify.

(C) The component 4 was added to the emulsion obtained in the step (B), then the components 9 and 10 were further added, and the mixture was homogenized.

It was confirmed that the oil-in-water UV-protection cream obtained as above spread lightly, was refreshing, was free from tackiness and oiliness, had transparency and excellent make-up lasting properties, had no change with temperature or time, and had very excellent usability and stability.

INDUSTRIAL APPLICABILITY

The present invention can provide an olefin wax, which has reactivity to general hydrogen silicone having one or more SiH bonds in one molecule, and an inexpensive silicone-modified wax having a high-melting point using the olefin wax. The novel silicone-modified polyolefin wax of the present invention shows moldability, releasability and lubricity equal to or higher than those of a mixture of an unreactive olefin wax and silicone, and exhibits excellent printability and sealing properties. Therefore, the silicone-modified polyolefin wax can have both of the properties of silicone, such as heat resistance, gas permeability and electrical properties, and the properties of thermoplastic resins. By the use of the silicone-modified polyolefin wax alone or by the addition thereof to other thermoplastic resins, organic rubbers or engineering plastics, there can be improved surface slip characteristics, releasabily, impact resistance and the like. Moreover, the silicone-modified polyolefin wax is effective also as a compatibilizing agent for elastomers. By the addition of the silicone-modified polyolefin wax to polyethylene or polypropylene that is used as a food packaging film, it can be expected that the silicone-modified polyolefin wax serves as an anti-blocking agent that does not impair film transparency, to enhance lubricating properties.

The silicone-modified polyolefin wax contains no free silicone oil, so that even if it is internally added to a toner used in a copy machine or the like, aggregation of toner with time does not take place. Therefore, the silicone-modified polyolefin wax of the present invention is particularly effective as a wax that is internally added to a toner, and besides, it can be used also as a surface modifier such as car wax, a release agent for various purposes, or a lubricity imparting agent. The silicone-modified polyolefin wax has a high melting point and can make oil agents, particularly, a silicone oil, smooth solids. Accordingly, by the addition of the silicone-modified polyolefin wax to cosmetics, there can be obtained cosmetics having excellent usability. The cosmetics of the present invention give lightly-spreading feeling and refreshing feeling when used, specifically, they are free from tackiness and heaviness when painted, are dry and spread lightly, and the skin after painted is dry and smooth to the touch. Moreover, the cosmetics have strong repellency against sweat and water, have excellent usability, specifically, ability of imparting softness, smoothness, emollient effect and natural gloss without impairing suitable transpiration of moisture by application of them, and have favorable temporal stability.

The invention claimed is:

1. A silicone-modified olefin wax (B) obtained by addition-reaction of a hydrogen silicone having one or more SiH bonds in one molecule to an olefin wax (A) in the presence of a catalyst, wherein the olefin wax is a copolymer (A1) obtained by copolymerizing ethylene and at least one diene or a copolymer (A2) obtained by copolymerizing ethylene, at least one olefin selected from α-olefins of 3 to 12 carbon atoms and at least one diene, wherein
(i) the content of unsaturated groups per one molecule is in the range of 0.5 to 3.0 groups,
(ii) the density is in the range of 870 to 980 kg/m³,
(iii) the melting point is in the range of 70 to 130° C.,
(iv) the number-average molecular weight is in the range of 400 to 5,000, and
(v) the ratio (Mw/Mn) of the weight-average molecular weight to the number-average molecular weight is not more than 4.0.

2. A silicone-modified room temperature-solidifying composition (D) comprising the silicone-modified olefin wax (B) of claim 1 in an amount of 5 to 95% by mass and an oil agent (C) in an amount of 95 to 5% by mass.

3. A cosmetic comprising the silicone-modified olefin wax (B) of claim 1.

4. A cosmetic comprising the silicone-modified room temperature-solidifying composition (D) of claim 2, wherein at least a part of the oil agent (C) is liquid at ordinary temperature.

5. A cosmetic comprising the silicone-modified room temperature-solidifying composition (D) of claim 2, wherein at least a part of the oil agent (C) is a solid oil agent having a melting point of not lower than 50° C.

6. A cosmetic comprising the silicone-modified room temperature-solidifying composition (D) of claim 2, wherein at least a part of the oil agent (C) is a linear, branched or cyclic silicone oil represented by the following formula:

wherein $R^1$ is a hydrogen atom, an alkyl group or a fluorine-substituted alkyl group of 1 to 30 carbon atoms, an aryl group of 6 to 30 carbon atoms or an aralkyl group of 7 to 30 carbon atoms, and "a" is a number satisfying the condition of $0 \leq a \leq 2.5$.

7. A cosmetic comprising the silicone-modified room temperature-solidifying composition (D) of claim 2, wherein at least a part of the oil agent (C) has a fluorine atom or an amino group.

8. The cosmetic as claimed in claim 3, which further comprises water (E).

9. The cosmetic as claimed in claim 3, which further comprises a compound (F) having an alcoholic hydroxyl group in the molecular structure.

10. The cosmetic as claimed in claim 9, wherein the compound (F) having an alcoholic hydroxyl group in the molecular structure is a water-soluble monohydric alcohol and/or a water-soluble polyhydric alcohol.

11. The cosmetic as claimed in claim 3, which further comprises a water-soluble or water-swelling high-molecular substance (G).

12. The cosmetic as claimed in claim 3, which further comprises a powder (H1) and/or a colorant (H2).

13. The cosmetic as claimed in claim 12, wherein at least a part of the powder (H1) and/or the colorant (H2) is a crosslinked spherical dimethylpolysiloxane fine powder having a structure in which dimethylpolysiloxane is crosslinked, a crosslinked spherical polymethylsilsesquioxane fine powder, hydrophobic silica or a fine powder obtained by coating a surface of a crosslinked spherical polysiloxane rubber with polymethylsilsesquioxane particles.

14. The cosmetic as claimed in claim 12, wherein at least a part of the powder (H1) and/or the colorant (H2) has a fluorine atom.

15. The cosmetic as claimed in claim 3, which further comprises a surface active agent (I).

16. The cosmetic as claimed in claim 15, wherein the surface active agent (I) is linear or branched silicone having a polyoxyalkylene chain in the molecule and/or linear or branched silicone having a polyglycerin chain in the molecule.

17. The cosmetic as claimed in claim 15, wherein the surface active agent (I) has a hydrophilic-lipophilic balance (HLB) of 2 to 8.

18. The cosmetic as claimed in claim 3, which further comprises a crosslinkable organopolysiloxane (J).

19. The cosmetic as claimed in claim 18, wherein the crosslinkable organopolysiloxane (J) is a crosslinkable organopolysiloxane which contains low-viscosity silicone having a viscosity of 0.65 to 10.0 mm²/sec (25° C.) in an amount of not less than its own weight to swell.

20. The cosmetic as claimed in claim 18, wherein the crosslinkable organopolysiloxane (J) is capable of forming a crosslinked structure by the reaction of a hydrogen atom directly bonded to a silicon atom of the organopolysiloxane (J) with a crosslinking agent having two or more vinyl reaction sites in the molecule.

21. The cosmetic as claimed claim 18, wherein the crosslinkable organopolysiloxane (J) contains at least one site selected from the group consisting of polyoxyalkylene, polyglycerin, alkyl, alkenyl, aryl and fluoroalkyl in the crosslinkable molecule.

22. The cosmetic as claimed in claim 3, which further comprises a silicone resin (K).

23. The cosmetic as claimed in claim 22, wherein the silicone resin (K) is an acrylic silicone resin.

24. The cosmetic as claimed in claim 23, wherein the silicone resin (K) is an acrylic silicone resin containing at least one site selected from the group consisting of pyrrolidone, long-chain alkyl, polyoxyalkylene, fluoroalkyl and anions of carboxylic acids or the like in the molecule.

25. The cosmetic as claimed in claim 22, wherein the silicone resin (K) is a silicone network compound selected from a silicone network compound (MQ) consisting essentially of a monofunctional siloxy group and a tetrafunctional siloxy group; a silicone network compound (MDQ) consisting essentially of a monofunctional siloxy group, a bifunctional siloxy group and a tetrafunctional siloxy group; a silicone network compound (MT) consisting essentially of a monofunctional siloxy group and a trifunctional siloxy group; a silicone network compound (MDT) consisting essentially of a monofunctional siloxy group, a bifunctional siloxy group and a trifunctional siloxy group; and a silicone network compound (MDTQ) consisting essentially of a monofunctional siloxy group, a bifunctional siloxy group, a trifunctional siloxy group and a tetrafunctional siloxy group.

26. The cosmetic as claimed in claim 22, wherein the silicone resin (K) is a silicone network compound containing at least one site selected from the group consisting of pyrrolidone, long-chain alkyl, polyoxyalkylene, fluoroalkyl and an amino group in the molecule.

27. A skin care cosmetic comprising the cosmetic of claim 3 as at least a part of constituents.

28. A make-up cosmetic comprising the cosmetic of claim 3 as at least a part of constituents.

29. A hair cosmetic comprising the cosmetic of claim 3 as at least a part of constituents.

30. An antiperspirant cosmetic comprising the cosmetic of claim 3 as at least a part of constituents.

31. An ultraviolet protective cosmetic comprising the cosmetic of claim 3 as at least a part of constituents.

32. The cosmetic as claimed in claim 3, which is in liquid, emulsion, cream, solid, paste, gel, powder, pressed, multilayer, mousse, spray, stick or pencil form.

* * * * *